(12) United States Patent
Shin et al.

(10) Patent No.: US 10,308,916 B2
(45) Date of Patent: Jun. 4, 2019

(54) OMEGA-TRANSAMINASE MUTANTS WITH ACTIVITY IMPROVEMENTS TOWARD KETONES AND METHODS FOR PRODUCING OPTICALLY PURE AMINES

(71) Applicant: Industry-Academic Cooperation Foundation, Yonsei University, Seoul (KR)

(72) Inventors: Jong-Shik Shin, Seoul (KR); Eul-Soo Park, Gyeonggi-do (KR); Sang-woo Han, Gyeonggi-do (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 49 days.

(21) Appl. No.: 15/094,625

(22) Filed: Apr. 8, 2016

(65) Prior Publication Data
US 2016/0298092 A1 Oct. 13, 2016

(30) Foreign Application Priority Data

Apr. 8, 2015 (KR) ........................ 10-2015-0049656

(51) Int. Cl.
*C12N 9/10* (2006.01)
*C12P 13/00* (2006.01)
*C12N 15/09* (2006.01)
*C12N 15/00* (2006.01)

(52) U.S. Cl.
CPC ........... *C12N 9/1096* (2013.01); *C12N 15/09* (2013.01); *C12P 13/001* (2013.01); *C12Y 206/01018* (2013.01)

(58) Field of Classification Search
None
See application file for complete search history.

(56) References Cited

PUBLICATIONS

Branden et al. Introduction to Protein Structure, Garland Publishing Inc., New York, p. 247, 1991.*
Murphy. T35443. EMBL. 1993.*
Sambrook et al. Molecular Cloning, 1989, Cold Spring Harbor Laboratory Press, pp. 8.46-8.52 and pp. 11.2-11.19.*
Finan. Q92WD3. UniProtKB. 2001.*
Studer Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Savile, C., et al., "Biocatalytic Asymmetric Synthesis of Chiral Amines from Ketones Applied to Sitagliptin Manufacture," Science, Jul. 16, 2010, vol. 329, pp. 305-309.
Han, S.H., et al., "Mechanism-Guided Engineering of w-Transaminase to Accelerate Reductive Amination of Ketones," Adv. Synth. Catal., 2015, vol. 357, pp. 1732-1740.

* cited by examiner

*Primary Examiner* — Yong D Pak
(74) *Attorney, Agent, or Firm* — Duane Morris LLP; Gregory M. Lefkowitz; Jason M. Nolan

(57) ABSTRACT

Provided is an omega-transaminase mutant with improved activity using a point mutation in an active site of an omega-transaminase. Specifically, provided is a method for improving activity and extending a substrate spectrum of omega-transaminase by introducing a point mutation into a wild-type omega-transaminase rendered by replacing tryptophan at position 58 with the other amino acid.

8 Claims, 3 Drawing Sheets
Specification includes a Sequence Listing.

SEQUENCE LISTING

<160> NUMBER OF SEQ ID NOS: 30

<210> SEQ ID NO 1
<211> LENGTH: 456
<212> TYPE: PRT
<213> ORGANISM: Ochrobactrum anthropi

<400> SEQUENCE: 1

```
Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Trp Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
```

```
            210                 215                 220
Glu Pro Val Met Gly Ala Gly Val Val Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
                260                 265                 270

Ser Gln Thr Phe Asp Met Lys Pro Asp Ile Leu Val Met Ser Lys Gln
                275                 280                 285

Leu Ser Ser Ser Tyr Leu Pro Ile Ser Ala Phe Leu Ile Asn Glu Arg
            290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
                340                 345                 350

Asp Arg Gly Thr Tyr Met Gln Lys Arg Leu Arg Glu Leu Gln Asp His
                355                 360                 365

Pro Leu Val Gly Glu Val Arg Gly Val Gly Leu Ile Ala Gly Val Glu
                370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
                435                 440                 445

Asp Val Gln Ala Ser Leu Thr Arg
            450                 455

<210> SEQ ID NO 2
<211> LENGTH: 456
<212> TYPE: PRT
<213> ORGANISM: Artificial Sequence
<220> FEATURE:
<223> OTHER INFORMATION: OATA W58L

<400> SEQUENCE: 2

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Leu Leu Ser Val Gly Val Gly Phe
50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
```

```
                   115                 120                 125
Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 3
<211> LENGTH: 456
<212> TYPE: PRT
<213> ORGANISM: Artificial Sequence
<220> FEATURE:
<223> OTHER INFORMATION: OATA W58A

<400> SEQUENCE: 3

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
```

```
                    20                  25                  30
Val Ile Glu Arg Gly Asp Gly Ile Tyr Val Glu Asp Val Ser Gly Lys
                35                  40                  45
Arg Tyr Ile Glu Ala Met Ser Gly Leu Ala Ser Val Gly Val Gly Phe
             50                  55                  60
Ser Glu Pro Arg Leu Ala Glu Ala Ala Arg Gln Met Lys Lys Leu
 65                  70                  75                  80
Pro Phe Tyr His Thr Phe Ser Tyr Arg Ser His Gly Pro Val Ile Asp
                 85                  90                  95
Leu Ala Glu Lys Leu Val Ser Met Ala Pro Val Pro Met Ser Lys Ala
                100                 105                 110
Tyr Phe Thr Asn Ser Gly Ser Glu Ala Asn Asp Thr Val Val Lys Leu
                115                 120                 125
Ile Trp Tyr Arg Ser Asn Ala Leu Gly Glu Pro Glu Arg Lys Lys Ile
                130                 135                 140
Ile Ser Arg Lys Arg Gly Tyr His Gly Val Thr Ile Ala Ser Ala Ser
145                 150                 155                 160
Leu Thr Gly Leu Pro Asn Asn His Arg Ser Phe Asp Leu Pro Ile Asp
                165                 170                 175
Arg Ile Leu His Thr Gly Cys Pro His Phe Tyr Arg Glu Gly Gln Ala
                180                 185                 190
Gly Glu Ser Glu Glu Gln Phe Ala Thr Arg Leu Ala Asp Glu Leu Glu
                195                 200                 205
Gln Leu Ile Ile Ala Glu Gly Pro His Thr Ile Ala Ala Phe Ile Gly
                210                 215                 220
Glu Pro Val Met Gly Ala Gly Gly Val Val Pro Pro Lys Thr Tyr
225                 230                 235                 240
Trp Glu Lys Val Gln Ala Val Leu Lys Arg Tyr Asp Ile Leu Leu Ile
                245                 250                 255
Ala Asp Glu Val Ile Cys Gly Phe Gly Arg Thr Gly Asn Leu Phe Gly
                260                 265                 270
Ser Gln Thr Phe Asp Met Lys Pro Asp Ile Leu Val Met Ser Lys Gln
                275                 280                 285
Leu Ser Ser Ser Tyr Leu Pro Ile Ser Ala Phe Leu Ile Asn Glu Arg
                290                 295                 300
Val Tyr Ala Pro Ile Ala Glu Glu Ser His Lys Ile Gly Thr Leu Gly
305                 310                 315                 320
Thr Gly Phe Thr Ala Ser Gly His Pro Val Ala Ala Val Ala Leu
                325                 330                 335
Glu Asn Leu Ala Ile Ile Glu Glu Arg Asp Leu Val Ala Asn Ala Arg
                340                 345                 350
Asp Arg Gly Thr Tyr Met Gln Lys Arg Leu Arg Glu Leu Gln Asp His
                355                 360                 365
Pro Leu Val Gly Glu Val Arg Gly Val Gly Leu Ile Ala Gly Val Glu
                370                 375                 380
Leu Val Thr Asp Lys Gln Ala Lys Thr Gly Leu Glu Pro Thr Gly Ala
385                 390                 395                 400
Leu Gly Ala Lys Ala Asn Ala Val Leu Gln Glu Arg Gly Val Ile Ser
                405                 410                 415
Arg Ala Met Gly Asp Thr Leu Ala Phe Cys Pro Pro Leu Ile Ile Asn
                420                 425                 430
Asp Gln Gln Val Asp Thr Met Val Ser Ala Leu Glu Ala Thr Leu Asn
                435                 440                 445
```

Asp Val Gln Ala Ser Leu Thr Arg
    450             455

<210> SEQ ID NO 4
<211> LENGTH: 456
<212> TYPE: PRT
<213> ORGANISM: Artificial Sequence
<220> FEATURE:
<223> OTHER INFORMATION: OATA W58M

<400> SEQUENCE: 4

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Met Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

```
Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 5
<211> LENGTH: 456
<212> TYPE: PRT
<213> ORGANISM: Artificial Sequence
<220> FEATURE:
<223> OTHER INFORMATION: OATA W58V

<400> SEQUENCE: 5

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Val Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255
```

```
Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
            325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
            370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
            435                 440                 445

Asp Val Gln Ala Ser Leu Thr Arg
        450                 455

<210> SEQ ID NO 6
<211> LENGTH: 456
<212> TYPE: PRT
<213> ORGANISM: Artificial Sequence
<220> FEATURE:
<223> OTHER INFORMATION: OATA W58I

<400> SEQUENCE: 6

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Ile Ser Val Gly Val Gly Phe
50                  55                  60

Ser Glu Pro Arg Leu Ala Glu Ala Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160
```

```
Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 7
<211> LENGTH: 456
<212> TYPE: PRT
<213> ORGANISM: Artificial Sequence
<220> FEATURE:
<223> OTHER INFORMATION: OATA W58P

<400> SEQUENCE: 7

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Leu Pro Ser Val Gly Val Gly Phe
        50                  55                  60
```

```
Ser Glu Pro Arg Leu Ala Glu Ala Ala Arg Gln Met Lys Lys Leu
 65                  70                  75                  80

Pro Phe Tyr His Thr Phe Ser Tyr Arg Ser His Gly Pro Val Ile Asp
                 85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
                115                 120                 125

Ile Trp Tyr Arg Ser Asn Ala Leu Gly Glu Pro Glu Arg Lys Lys Ile
                130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
                180                 185                 190

Gly Glu Ser Glu Glu Gln Phe Ala Thr Arg Leu Ala Asp Glu Leu Glu
                195                 200                 205

Gln Leu Ile Ile Ala Glu Gly Pro His Thr Ile Ala Ala Phe Ile Gly
                210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
                260                 265                 270

Ser Gln Thr Phe Asp Met Lys Pro Asp Ile Leu Val Met Ser Lys Gln
                275                 280                 285

Leu Ser Ser Ser Tyr Leu Pro Ile Ser Ala Phe Leu Ile Asn Glu Arg
                290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
                340                 345                 350

Asp Arg Gly Thr Tyr Met Gln Lys Arg Leu Arg Glu Leu Gln Asp His
                355                 360                 365

Pro Leu Val Gly Glu Val Arg Gly Val Gly Leu Ile Ala Gly Val Glu
                370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
                435                 440                 445

Asp Val Gln Ala Ser Leu Thr Arg
450                 455

<210> SEQ ID NO 8
<211> LENGTH: 456
```

<212> TYPE: PRT
<213> ORGANISM: Artificial Sequence
<220> FEATURE:
<223> OTHER INFORMATION: OATA W58G

<400> SEQUENCE: 8

```
Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Gly Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380
```

```
Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
        450                 455

<210> SEQ ID NO 9
<211> LENGTH: 456
<212> TYPE: PRT
<213> ORGANISM: Artificial Sequence
<220> FEATURE:
<223> OTHER INFORMATION: OATA W58F

<400> SEQUENCE: 9

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Phe Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285
```

-continued

```
Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
                355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
            435                 440                 445

Asp Val Gln Ala Ser Leu Thr Arg
    450                 455

<210> SEQ ID NO 10
<211> LENGTH: 456
<212> TYPE: PRT
<213> ORGANISM: Artificial Sequence
<220> FEATURE:
<223> OTHER INFORMATION: OATA W58S

<400> SEQUENCE: 10

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Leu Ser Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
    115                 120                 125

Ile Trp Tyr Arg Ser Asn Ala Leu Gly Glu Pro Glu Arg Lys Lys Ile
130                 135                 140

Ile Ser Arg Lys Arg Gly Tyr His Gly Val Thr Ile Ala Ser Ala Ser
                145                 150                 155                 160

Leu Thr Gly Leu Pro Asn Asn His Arg Ser Phe Asp Leu Pro Ile Asp
            165                 170                 175

Arg Ile Leu His Thr Gly Cys Pro His Phe Tyr Arg Glu Gly Gln Ala
    180                 185                 190
```

```
Gly Glu Ser Glu Glu Gln Phe Ala Thr Arg Leu Ala Asp Glu Leu Glu
            195                 200                 205

Gln Leu Ile Ile Ala Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
    275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
    435                 440                 445

Asp Val Gln Ala Ser Leu Thr Arg
    450                 455

<210> SEQ ID NO 11
<211> LENGTH: 456
<212> TYPE: PRT
<213> ORGANISM: Artificial Sequence
<220> FEATURE:
<223> OTHER INFORMATION: OATA W58T

<400> SEQUENCE: 11

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Leu Thr Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95
```

```
Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
        130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
450                 455
```

<210> SEQ ID NO 12
<211> LENGTH: 456
<212> TYPE: PRT
<213> ORGANISM: Artificial Sequence
<220> FEATURE:
<223> OTHER INFORMATION: OATA W58C

<400> SEQUENCE: 12

```
Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Cys Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
        130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
            245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
            325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
            405                 410                 415

Arg Ala Met Gly Asp Thr Leu Ala Phe Cys Pro Pro Leu Ile Ile Asn
```

Asp Gln Gln Val Asp Thr Met Val Ser Ala Leu Glu Ala Thr Leu Asn
            420                 425                 430

Asp Val Gln Ala Ser Leu Thr Arg
        435                 440

<210> SEQ ID NO 13
<211> LENGTH: 456
<212> TYPE: PRT
<213> ORGANISM: Artificial Sequence
<220> FEATURE:
<223> OTHER INFORMATION: OATA W58Q

<400> SEQUENCE: 13

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Gln Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Ala Val Ala Leu

```
                  325                 330                 335
Glu Asn Leu Ala Ile Ile Glu Glu Arg Asp Leu Val Ala Asn Ala Arg
                340                 345                 350
Asp Arg Gly Thr Tyr Met Gln Lys Arg Leu Arg Glu Leu Gln Asp His
            355                 360                 365
Pro Leu Val Gly Glu Val Arg Gly Val Gly Leu Ile Ala Gly Val Glu
        370                 375                 380
Leu Val Thr Asp Lys Gln Ala Lys Thr Gly Leu Glu Pro Thr Gly Ala
385                 390                 395                 400
Leu Gly Ala Lys Ala Asn Ala Val Leu Gln Glu Arg Gly Val Ile Ser
                405                 410                 415
Arg Ala Met Gly Asp Thr Leu Ala Phe Cys Pro Pro Leu Ile Ile Asn
                420                 425                 430
Asp Gln Gln Val Asp Thr Met Val Ser Ala Leu Glu Ala Thr Leu Asn
            435                 440                 445
Asp Val Gln Ala Ser Leu Thr Arg
        450                 455

<210> SEQ ID NO 14
<211> LENGTH: 456
<212> TYPE: PRT
<213> ORGANISM: Artificial Sequence
<220> FEATURE:
<223> OTHER INFORMATION: OATA W58N

<400> SEQUENCE: 14

Met Thr Ala Gln Pro Asn Ser Leu Glu Ala Arg Asp Ile Arg Tyr His
1               5                   10                  15
Leu His Ser Tyr Thr Asp Ala Val Arg Leu Glu Ala Glu Gly Pro Leu
                20                  25                  30
Val Ile Glu Arg Gly Asp Gly Ile Tyr Val Glu Asp Val Ser Gly Lys
            35                  40                  45
Arg Tyr Ile Glu Ala Met Ser Gly Leu Asn Ser Val Gly Val Gly Phe
        50                  55                  60
Ser Glu Pro Arg Leu Ala Glu Ala Ala Arg Gln Met Lys Lys Leu
65                  70                  75                  80
Pro Phe Tyr His Thr Phe Ser Tyr Arg Ser His Gly Pro Val Ile Asp
                85                  90                  95
Leu Ala Glu Lys Leu Val Ser Met Ala Pro Val Pro Met Ser Lys Ala
                100                 105                 110
Tyr Phe Thr Asn Ser Gly Ser Glu Ala Asn Asp Thr Val Val Lys Leu
            115                 120                 125
Ile Trp Tyr Arg Ser Asn Ala Leu Gly Glu Pro Glu Arg Lys Lys Ile
        130                 135                 140
Ile Ser Arg Lys Arg Gly Tyr His Gly Val Thr Ile Ala Ser Ala Ser
145                 150                 155                 160
Leu Thr Gly Leu Pro Asn Asn His Arg Ser Phe Asp Leu Pro Ile Asp
                165                 170                 175
Arg Ile Leu His Thr Gly Cys Pro His Phe Tyr Arg Glu Gly Gln Ala
                180                 185                 190
Gly Glu Ser Glu Glu Gln Phe Ala Thr Arg Leu Ala Asp Glu Leu Glu
            195                 200                 205
Gln Leu Ile Ile Ala Glu Gly Pro His Thr Ile Ala Ala Phe Ile Gly
        210                 215                 220
Glu Pro Val Met Gly Ala Gly Gly Val Val Val Pro Pro Lys Thr Tyr
```

```
                225                 230                 235                 240
Trp Glu Lys Val Gln Ala Val Leu Lys Arg Tyr Asp Ile Leu Leu Ile
                    245                 250                 255

Ala Asp Glu Val Ile Cys Gly Phe Gly Arg Thr Gly Asn Leu Phe Gly
                260                 265                 270

Ser Gln Thr Phe Asp Met Lys Pro Asp Ile Leu Val Met Ser Lys Gln
            275                 280                 285

Leu Ser Ser Tyr Leu Pro Ile Ser Ala Phe Leu Ile Asn Glu Arg
        290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
                340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
            435                 440                 445

Asp Val Gln Ala Ser Leu Thr Arg
        450                 455

<210> SEQ ID NO 15
<211> LENGTH: 456
<212> TYPE: PRT
<213> ORGANISM: Artificial Sequence
<220> FEATURE:
<223> OTHER INFORMATION: OATA W58Y

<400> SEQUENCE: 15

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Leu Tyr Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
```

```
                130                 135                 140
Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 16
<211> LENGTH: 456
<212> TYPE: PRT
<213> ORGANISM: Artificial Sequence
<220> FEATURE:
<223> OTHER INFORMATION: OATA W58D

<400> SEQUENCE: 16

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
```

```
            35                  40                  45
Arg Tyr Ile Glu Ala Met Ser Gly Leu Asp Ser Val Gly Val Gly Phe
 50                  55                  60

Ser Glu Pro Arg Leu Ala Glu Ala Ala Arg Gln Met Lys Lys Leu
 65                  70                  75                  80

Pro Phe Tyr His Thr Phe Ser Tyr Arg Ser His Gly Pro Val Ile Asp
                 85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
                115                 120                 125

Ile Trp Tyr Arg Ser Asn Ala Leu Gly Glu Pro Glu Arg Lys Lys Ile
130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
                180                 185                 190

Gly Glu Ser Glu Glu Gln Phe Ala Thr Arg Leu Ala Asp Glu Leu Glu
                195                 200                 205

Gln Leu Ile Ile Ala Glu Gly Pro His Thr Ile Ala Ala Phe Ile Gly
210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
                260                 265                 270

Ser Gln Thr Phe Asp Met Lys Pro Asp Ile Leu Val Met Ser Lys Gln
                275                 280                 285

Leu Ser Ser Ser Tyr Leu Pro Ile Ser Ala Phe Leu Ile Asn Glu Arg
290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
                340                 345                 350

Asp Arg Gly Thr Tyr Met Gln Lys Arg Leu Arg Glu Leu Gln Asp His
                355                 360                 365

Pro Leu Val Gly Glu Val Arg Gly Val Gly Leu Ile Ala Gly Val Glu
                370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
                435                 440                 445

Asp Val Gln Ala Ser Leu Thr Arg
450                 455
```

<210> SEQ ID NO 17
<211> LENGTH: 456
<212> TYPE: PRT
<213> ORGANISM: Artificial Sequence
<220> FEATURE:
<223> OTHER INFORMATION: OATA W58E

<400> SEQUENCE: 17

```
Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Glu Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365
```

-continued

```
Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Leu Ile Ile Asn
                420                 425                 430

Asp Gln Gln Val Asp Thr Met Val Ser Ala Leu Glu Ala Thr Leu Asn
                435                 440                 445

Asp Val Gln Ala Ser Leu Thr Arg
    450                 455
```

<210> SEQ ID NO 18
<211> LENGTH: 456
<212> TYPE: PRT
<213> ORGANISM: Artificial Sequence
<220> FEATURE:
<223> OTHER INFORMATION: OATA Y20A/W58A

<400> SEQUENCE: 18

```
Met Thr Ala Gln Pro Asn Ser Leu Glu Ala Arg Asp Ile Arg Tyr His
1               5                   10                  15

Leu His Ser Ala Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Leu Ala Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
                180                 185                 190

Gly Glu Ser Glu Glu Gln Phe Ala Thr Arg Leu Ala Asp Glu Leu Glu
            195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
                260                 265                 270
```

```
Ser Gln Thr Phe Asp Met Lys Pro Asp Ile Leu Val Met Ser Lys Gln
        275                 280                 285

Leu Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
                340                 345                 350

Asp Arg Gly Thr Tyr Met Gln Lys Arg Leu Arg Glu Leu Gln Asp His
                355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
                435                 440                 445

Asp Val Gln Ala Ser Leu Thr Arg
450                 455

<210> SEQ ID NO 19
<211> LENGTH: 456
<212> TYPE: PRT
<213> ORGANISM: Artificial Sequence
<220> FEATURE:
<223> OTHER INFORMATION: OATA M54A/W58A

<400> SEQUENCE: 19

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
                35                  40                  45

Arg Tyr Ile Glu Ala Ala Ser Gly Leu Ala Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
                115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175
```

```
Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 20
<211> LENGTH: 456
<212> TYPE: PRT
<213> ORGANISM: Artificial Sequence
<220> FEATURE:
<223> OTHER INFORMATION: OATA L57A/W58A

<400> SEQUENCE: 20

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Ala Ala Ser Val Gly Val Gly Phe
    50                  55                  60

Ser Glu Pro Arg Leu Ala Glu Ala Ala Arg Gln Met Lys Lys Leu
65                  70                  75                  80
```

```
Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 21
<211> LENGTH: 456
<212> TYPE: PRT
<213> ORGANISM: Artificial Sequence
<220> FEATURE:
```

<223> OTHER INFORMATION: OATA W58A/F86A

<400> SEQUENCE: 21

```
Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Ala Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Ala Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400
```

```
Leu Gly Ala Lys Ala Asn Ala Val Leu Gln Glu Arg Gly Val Ile Ser
            405                 410                 415

Arg Ala Met Gly Asp Thr Leu Ala Phe Cys Pro Pro Leu Ile Ile Asn
        420                 425                 430

Asp Gln Gln Val Asp Thr Met Val Ser Ala Leu Glu Ala Thr Leu Asn
            435                 440                 445

Asp Val Gln Ala Ser Leu Thr Arg
        450                 455

<210> SEQ ID NO 22
<211> LENGTH: 456
<212> TYPE: PRT
<213> ORGANISM: Artificial Sequence
<220> FEATURE:
<223> OTHER INFORMATION: OATA W58A/V154A

<400> SEQUENCE: 22

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Ala Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Ala Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300
```

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
        370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
            435                 440                 445

Asp Val Gln Ala Ser Leu Thr Arg
    450                 455

<210> SEQ ID NO 23
<211> LENGTH: 456
<212> TYPE: PRT
<213> ORGANISM: Artificial Sequence
<220> FEATURE:
<223> OTHER INFORMATION: OATA W58A/V233A

<400> SEQUENCE: 23

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Ala Ser Val Gly Val Gly Phe
50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
210                 215                 220

Glu Pro Val Met Gly Ala Gly Ala Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Gly Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 24
<211> LENGTH: 456
<212> TYPE: PRT
<213> ORGANISM: Artificial Sequence
<220> FEATURE:
<223> OTHER INFORMATION: OATA W58A/I261A

<400> SEQUENCE: 24

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Ala Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

```
Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ala Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
        355                 360                 365

Pro Leu Val Gly Glu Val Arg Gly Val Gly Leu Ile Ala Gly Val Glu
    370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455

<210> SEQ ID NO 25
<211> LENGTH: 456
<212> TYPE: PRT
<213> ORGANISM: Artificial Sequence
<220> FEATURE:
<223> OTHER INFORMATION: OATA W58A/T324A

<400> SEQUENCE: 25

Met Thr Ala Gln Pro Asn Ser Leu Glu Ala Arg Asp Ile Arg Tyr His
1               5                   10                  15
```

-continued

```
Leu His Ser Tyr Thr Asp Ala Val Arg Leu Glu Ala Glu Gly Pro Leu
                20                  25                  30
Val Ile Glu Arg Gly Asp Gly Ile Tyr Val Glu Asp Val Ser Gly Lys
         35                  40                  45
Arg Tyr Ile Glu Ala Met Ser Gly Leu Ala Ser Val Gly Val Gly Phe
 50                  55                  60
Ser Glu Pro Arg Leu Ala Glu Ala Ala Arg Gln Met Lys Lys Leu
 65                  70                  75                  80
Pro Phe Tyr His Thr Phe Ser Tyr Arg Ser His Gly Pro Val Ile Asp
                 85                  90                  95
Leu Ala Glu Lys Leu Val Ser Met Ala Pro Val Pro Met Ser Lys Ala
             100                 105                 110
Tyr Phe Thr Asn Ser Gly Ser Glu Ala Asn Asp Thr Val Val Lys Leu
             115                 120                 125
Ile Trp Tyr Arg Ser Asn Ala Leu Gly Glu Pro Glu Arg Lys Lys Ile
         130                 135                 140
Ile Ser Arg Lys Arg Gly Tyr His Gly Val Thr Ile Ala Ser Ala Ser
145                 150                 155                 160
Leu Thr Gly Leu Pro Asn Asn His Arg Ser Phe Asp Leu Pro Ile Asp
                 165                 170                 175
Arg Ile Leu His Thr Gly Cys Pro His Phe Tyr Arg Glu Gly Gln Ala
             180                 185                 190
Gly Glu Ser Glu Glu Gln Phe Ala Thr Arg Leu Ala Asp Glu Leu Glu
             195                 200                 205
Gln Leu Ile Ile Ala Glu Gly Pro His Thr Ile Ala Ala Phe Ile Gly
         210                 215                 220
Glu Pro Val Met Gly Ala Gly Gly Val Val Pro Pro Lys Thr Tyr
225                 230                 235                 240
Trp Glu Lys Val Gln Ala Val Leu Lys Arg Tyr Asp Ile Leu Leu Ile
                 245                 250                 255
Ala Asp Glu Val Ile Cys Gly Phe Gly Arg Thr Gly Asn Leu Phe Gly
             260                 265                 270
Ser Gln Thr Phe Asp Met Lys Pro Asp Ile Leu Val Met Ser Lys Gln
             275                 280                 285
Leu Ser Ser Ser Tyr Leu Pro Ile Ser Ala Phe Leu Ile Asn Glu Arg
         290                 295                 300
Val Tyr Ala Pro Ile Ala Glu Glu Ser His Lys Ile Gly Thr Leu Gly
305                 310                 315                 320
Thr Gly Phe Ala Ala Ser Gly His Pro Val Ala Ala Val Ala Leu
                 325                 330                 335
Glu Asn Leu Ala Ile Ile Glu Glu Arg Asp Leu Val Ala Asn Ala Arg
             340                 345                 350
Asp Arg Gly Thr Tyr Met Gln Lys Arg Leu Arg Glu Leu Gln Asp His
             355                 360                 365
Pro Leu Val Gly Glu Val Arg Gly Val Gly Leu Ile Ala Gly Val Glu
         370                 375                 380
Leu Val Thr Asp Lys Gln Ala Lys Thr Gly Leu Glu Pro Thr Gly Ala
385                 390                 395                 400
Leu Gly Ala Lys Ala Asn Ala Val Leu Gln Glu Arg Gly Val Ile Ser
                 405                 410                 415
Arg Ala Met Gly Asp Thr Leu Ala Phe Cys Pro Pro Leu Ile Ile Asn
             420                 425                 430
Asp Gln Gln Val Asp Thr Met Val Ser Ala Leu Glu Ala Thr Leu Asn
```

435                 440                 445
Asp Val Gln Ala Ser Leu Thr Arg
    450                 455

<210> SEQ ID NO 26
<211> LENGTH: 456
<212> TYPE: PRT
<213> ORGANISM: Artificial Sequence
<220> FEATURE:
<223> OTHER INFORMATION: OATA W58A/I380A

<400> SEQUENCE: 26

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
        35                  40                  45

Arg Tyr Ile Glu Ala Met Ser Gly Leu Ala Ser Val Gly Val Gly Phe
    50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
        115                 120                 125

Ile Trp Tyr Arg Ser Asn Ala Leu Gly Glu Pro Glu Arg Lys Lys Ile
    130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
        195                 200                 205

Gln Leu Ile Ile Ala Glu Gly Pro His Thr Ile Ala Ala Phe Ile Gly
    210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
        275                 280                 285

Leu Ser Ser Ser Tyr Leu Pro Ile Ser Ala Phe Leu Ile Asn Glu Arg
    290                 295                 300

Val Tyr Ala Pro Ile Ala Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg

-continued

```
                340                 345                 350

Asp Arg Gly Thr Tyr Met Gln Lys Arg Leu Arg Glu Leu Gln Asp His
                355                 360                 365

Pro Leu Val Gly Glu Val Arg Gly Val Gly Leu Ala Ala Gly Val Glu
        370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
                435                 440                 445

Asp Val Gln Ala Ser Leu Thr Arg
                450                 455

<210> SEQ ID NO 27
<211> LENGTH: 456
<212> TYPE: PRT
<213> ORGANISM: Artificial Sequence
<220> FEATURE:
<223> OTHER INFORMATION: OATA L57A/W58A/V154A

<400> SEQUENCE: 27

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Ala Ala Ser Val Gly Val Gly Phe
        50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
                85                  90                  95

Leu Ala Glu Lys Leu Val Ser Met Ala Pro Val Pro Met Ser Lys Ala
                100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
        130                 135                 140

Ile Ser Arg Lys Arg Gly Tyr His Gly Ala Thr Ile Ala Ser Ala Ser
145                 150                 155                 160

Leu Thr Gly Leu Pro Asn Asn His Arg Ser Phe Asp Leu Pro Ile Asp
                165                 170                 175

Arg Ile Leu His Thr Gly Cys Pro His Phe Tyr Arg Glu Gly Gln Ala
                180                 185                 190

Gly Glu Ser Glu Glu Gln Phe Ala Thr Arg Leu Ala Asp Glu Leu Glu
            195                 200                 205

Gln Leu Ile Ile Ala Glu Gly Pro His Thr Ile Ala Ala Phe Ile Gly
        210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
```

```
            245                 250                 255
Ala Asp Glu Val Ile Cys Gly Phe Gly Arg Thr Gly Asn Leu Phe Gly
            260                 265                 270

Ser Gln Thr Phe Asp Met Lys Pro Asp Ile Leu Val Met Ser Lys Gln
            275                 280                 285

Leu Ser Ser Ser Tyr Leu Pro Ile Ser Ala Phe Leu Ile Asn Glu Arg
            290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
            370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
            435                 440                 445

Asp Val Gln Ala Ser Leu Thr Arg
450                 455

<210> SEQ ID NO 28
<211> LENGTH: 456
<212> TYPE: PRT
<213> ORGANISM: Artificial Sequence
<220> FEATURE:
<223> OTHER INFORMATION: OATA L57Q/W58N/I261L

<400> SEQUENCE: 28

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
            20                  25                  30

Val Ile Glu Arg Gly Asp Gly Ile Tyr Val Glu Asp Val Ser Gly Lys
            35                  40                  45

Arg Tyr Ile Glu Ala Met Ser Gly Gln Asn Ser Val Gly Val Gly Phe
        50                  55                  60

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
            85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
        130                 135                 140

Ile Ser Arg Lys Arg Gly Tyr His Gly Val Thr Ile Ala Ser Ala Ser
```

```
                145                 150                 155                 160
Leu Thr Gly Leu Pro Asn Asn His Arg Ser Phe Asp Leu Pro Ile Asp
                    165                 170                 175

Arg Ile Leu His Thr Gly Cys Pro His Phe Tyr Arg Glu Gly Gln Ala
                180                 185                 190

Gly Glu Ser Glu Glu Gln Phe Ala Thr Arg Leu Ala Asp Glu Leu Glu
            195                 200                 205

Gln Leu Ile Ile Ala Glu Gly Pro His Thr Ile Ala Ala Phe Ile Gly
        210                 215                 220

Glu Pro Val Met Gly Ala Gly Val Val Pro Pro Lys Thr Tyr
225                 230                 235                 240

Trp Glu Lys Val Gln Ala Val Leu Lys Arg Tyr Asp Ile Leu Leu Ile
                245                 250                 255

Ala Asp Glu Val Leu Cys Gly Phe Gly Arg Thr Gly Asn Leu Phe Gly
                260                 265                 270

Ser Gln Thr Phe Asp Met Lys Pro Asp Ile Leu Val Met Ser Lys Gln
            275                 280                 285

Leu Ser Ser Ser Tyr Leu Pro Ile Ser Ala Phe Leu Ile Asn Glu Arg
        290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
                325                 330                 335

Glu Asn Leu Ala Ile Ile Glu Glu Arg Asp Leu Val Ala Asn Ala Arg
                340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
        370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
                420                 425                 430

Asp Gln Gln Val Asp Thr Met Val Ser Ala Leu Glu Ala Thr Leu Asn
            435                 440                 445

Asp Val Gln Ala Ser Leu Thr Arg
    450                 455

<210> SEQ ID NO 29
<211> LENGTH: 456
<212> TYPE: PRT
<213> ORGANISM: Artificial Sequence
<220> FEATURE:
<223> OTHER INFORMATION: OATA L57C/W58L/I261A

<400> SEQUENCE: 29

Met Thr Ala Gln Pro Asn Ser Leu Glu Ala Arg Asp Ile Arg Tyr His
1               5                   10                  15

Leu His Ser Tyr Thr Asp Ala Val Arg Leu Glu Ala Glu Gly Pro Leu
                20                  25                  30

Val Ile Glu Arg Gly Asp Gly Ile Tyr Val Glu Asp Val Ser Gly Lys
            35                  40                  45

Arg Tyr Ile Glu Ala Met Ser Gly Cys Leu Ser Val Gly Val Gly Phe
```

Ser Glu Pro Arg Leu Ala Glu Ala Ala Arg Gln Met Lys Lys Leu
65                  70                  75                  80

Pro Phe Tyr His Thr Phe Ser Tyr Arg Ser His Gly Pro Val Ile Asp
            85                  90                  95

Leu Ala Glu Lys Leu Val Ser Met Ala Pro Val Pro Met Ser Lys Ala
            100                 105                 110

Tyr Phe Thr Asn Ser Gly Ser Glu Ala Asn Asp Thr Val Val Lys Leu
            115                 120                 125

Ile Trp Tyr Arg Ser Asn Ala Leu Gly Glu Pro Glu Arg Lys Lys Ile
            130                 135                 140

Ile Ser Arg Lys Arg Gly Tyr His Gly Val Thr Ile Ala Ser Ala Ser
145                 150                 155                 160

Leu Thr Gly Leu Pro Asn Asn His Arg Ser Phe Asp Leu Pro Ile Asp
            165                 170                 175

Arg Ile Leu His Thr Gly Cys Pro His Phe Tyr Arg Glu Gly Gln Ala
            180                 185                 190

Gly Glu Ser Glu Glu Gln Phe Ala Thr Arg Leu Ala Asp Glu Leu Glu
            195                 200                 205

Gln Leu Ile Ile Ala Glu Gly Pro His Thr Ile Ala Ala Phe Ile Gly
210                 215                 220

Glu Pro Val Met Gly Ala Gly Gly Val Val Pro Pro Lys Thr Tyr
225                 230                 235                 240

Trp Glu Lys Val Gln Ala Val Leu Lys Arg Tyr Asp Ile Leu Leu Ile
            245                 250                 255

Ala Asp Glu Val Ala Cys Gly Phe Gly Arg Thr Gly Asn Leu Phe Gly
            260                 265                 270

Ser Gln Thr Phe Asp Met Lys Pro Asp Ile Leu Val Met Ser Lys Gln
            275                 280                 285

Leu Ser Ser Ser Tyr Leu Pro Ile Ser Ala Phe Leu Ile Asn Glu Arg
            290                 295                 300

Val Tyr Ala Pro Ile Ala Glu Glu Ser His Lys Ile Gly Thr Leu Gly
305                 310                 315                 320

Thr Gly Phe Thr Ala Ser Gly His Pro Val Ala Ala Val Ala Leu
            325                 330                 335

Glu Asn Leu Ala Ile Ile Glu Glu Arg Asp Leu Val Ala Asn Ala Arg
            340                 345                 350

Asp Arg Gly Thr Tyr Met Gln Lys Arg Leu Arg Glu Leu Gln Asp His
            355                 360                 365

Pro Leu Val Gly Glu Val Arg Gly Val Gly Leu Ile Ala Gly Val Glu
            370                 375                 380

Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
            405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
            435                 440                 445

Asp Val Gln Ala Ser Leu Thr Arg
450                 455

<210> SEQ ID NO 30

```
<211> LENGTH: 456
<212> TYPE: PRT
<213> ORGANISM: Artificial Sequence
<220> FEATURE:
<223> OTHER INFORMATION: OATA W58D/I261A

<400> SEQUENCE: 30
```

| Met | Thr | Ala | Gln | Pro | Asn | Ser | Leu | Glu | Ala | Arg | Asp | Ile | Arg | Tyr | His |
|---|---|---|---|---|---|---|---|---|---|---|---|---|---|---|---|
| 1 | | | | 5 | | | | | 10 | | | | | 15 | |

| Leu | His | Ser | Tyr | Thr | Asp | Ala | Val | Arg | Leu | Glu | Ala | Glu | Gly | Pro | Leu |
| | | | 20 | | | | | 25 | | | | | 30 | | |

| Val | Ile | Glu | Arg | Gly | Asp | Gly | Ile | Tyr | Val | Glu | Asp | Val | Ser | Gly | Lys |
| | | 35 | | | | | 40 | | | | | 45 | | | |

| Arg | Tyr | Ile | Glu | Ala | Met | Ser | Gly | Leu | Asp | Ser | Val | Gly | Val | Gly | Phe |
| 50 | | | | | 55 | | | | | 60 | | | | | |

| Ser | Glu | Pro | Arg | Leu | Ala | Glu | Ala | Ala | Arg | Gln | Met | Lys | Lys | Leu |
| 65 | | | | 70 | | | | | 75 | | | | | 80 |

| Pro | Phe | Tyr | His | Thr | Phe | Ser | Tyr | Arg | Ser | His | Gly | Pro | Val | Ile | Asp |
| | | | 85 | | | | | 90 | | | | | 95 | | |

| Leu | Ala | Glu | Lys | Leu | Val | Ser | Met | Ala | Pro | Val | Pro | Met | Ser | Lys | Ala |
| | | | 100 | | | | | 105 | | | | | 110 | | |

| Tyr | Phe | Thr | Asn | Ser | Gly | Ser | Glu | Ala | Asn | Asp | Thr | Val | Val | Lys | Leu |
| | | | 115 | | | | | 120 | | | | | 125 | | |

| Ile | Trp | Tyr | Arg | Ser | Asn | Ala | Leu | Gly | Glu | Pro | Glu | Arg | Lys | Lys | Ile |
| | 130 | | | | | 135 | | | | | 140 | | | | |

| Ile | Ser | Arg | Lys | Arg | Gly | Tyr | His | Gly | Val | Thr | Ile | Ala | Ser | Ala | Ser |
| 145 | | | | | 150 | | | | | 155 | | | | | 160 |

| Leu | Thr | Gly | Leu | Pro | Asn | Asn | His | Arg | Ser | Phe | Asp | Leu | Pro | Ile | Asp |
| | | | | 165 | | | | | 170 | | | | | 175 | |

| Arg | Ile | Leu | His | Thr | Gly | Cys | Pro | His | Phe | Tyr | Arg | Glu | Gly | Gln | Ala |
| | | | 180 | | | | | 185 | | | | | 190 | | |

| Gly | Glu | Ser | Glu | Glu | Gln | Phe | Ala | Thr | Arg | Leu | Ala | Asp | Glu | Leu | Glu |
| | | 195 | | | | | 200 | | | | | 205 | | | |

| Gln | Leu | Ile | Ile | Ala | Glu | Gly | Pro | His | Thr | Ile | Ala | Ala | Phe | Ile | Gly |
| 210 | | | | | 215 | | | | | 220 | | | | | |

| Glu | Pro | Val | Met | Gly | Ala | Gly | Gly | Val | Val | Pro | Pro | Lys | Thr | Tyr |
| 225 | | | | | 230 | | | | | 235 | | | | | 240 |

| Trp | Glu | Lys | Val | Gln | Ala | Val | Leu | Lys | Arg | Tyr | Asp | Ile | Leu | Leu | Ile |
| | | | | 245 | | | | | 250 | | | | | 255 | |

| Ala | Asp | Glu | Val | Ala | Cys | Gly | Phe | Gly | Arg | Thr | Gly | Asn | Leu | Phe | Gly |
| | | | 260 | | | | | 265 | | | | | 270 | | |

| Ser | Gln | Thr | Phe | Asp | Met | Lys | Pro | Asp | Ile | Leu | Val | Met | Ser | Lys | Gln |
| | | 275 | | | | | 280 | | | | | 285 | | | |

| Leu | Ser | Ser | Ser | Tyr | Leu | Pro | Ile | Ser | Ala | Phe | Leu | Ile | Asn | Glu | Arg |
| | 290 | | | | | 295 | | | | | 300 | | | | |

| Val | Tyr | Ala | Pro | Ile | Ala | Glu | Glu | Ser | His | Lys | Ile | Gly | Thr | Leu | Gly |
| 305 | | | | | 310 | | | | | 315 | | | | | 320 |

| Thr | Gly | Phe | Thr | Ala | Ser | Gly | His | Pro | Val | Ala | Ala | Val | Ala | Leu |
| | | | | 325 | | | | | 330 | | | | | 335 |

| Glu | Asn | Leu | Ala | Ile | Ile | Glu | Gly | Arg | Asp | Leu | Val | Ala | Asn | Ala | Arg |
| | | | 340 | | | | | 345 | | | | | 350 | | |

| Asp | Arg | Gly | Thr | Tyr | Met | Gln | Lys | Arg | Leu | Arg | Glu | Leu | Gln | Asp | His |
| | | 355 | | | | | 360 | | | | | 365 | | | |

| Pro | Leu | Val | Gly | Glu | Val | Arg | Gly | Val | Gly | Leu | Ile | Ala | Gly | Val | Glu |
| | 370 | | | | | 375 | | | | | 380 | | | | |

```
Leu Val Thr Asp Lys Gln Ala Lys Thr Gly Leu Glu Pro Thr Gly Ala
385                 390                 395                 400

Leu Gly Ala Lys Ala Asn Ala Val Leu Gln Glu Arg Gly Val Ile Ser
                405                 410                 415

Arg Ala Met Gly Asp Thr Leu Ala Phe Cys Pro Pro Leu Ile Ile Asn
            420                 425                 430

Asp Gln Gln Val Asp Thr Met Val Ser Ala Leu Glu Ala Thr Leu Asn
        435                 440                 445

Asp Val Gln Ala Ser Leu Thr Arg
    450                 455
```

OMEGA-TRANSAMINASE MUTANTS WITH ACTIVITY IMPROVEMENTS TOWARD KETONES AND METHODS FOR PRODUCING OPTICALLY PURE AMINES

CROSS-REFERENCE TO RELATED APPLICATIONS

This application claims priority under 35 U.S.C. § 119 to Korean Patent Application No. 10-2015-0049656 filed on Apr. 8, 2015 in the Korean Intellectual Property Office, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 11, 2016, is named G1035-08001_HPC6645_sequence_list.txt and is 114,688 bytes in size.

BACKGROUND OF THE INVENTION

Field of the Invention

The present invention relates to omega-transaminase mutants with improved activity toward ketones and more specifically, to methods for efficient production of optically active amines using the omega-transaminase mutants with improved activity toward ketones produced by replacement of certain amino acids in active sites.

Description of the Related Art

At present, asymmetric synthesis of chiral compounds using biocatalytic synthesis attracts a great deal of attention as an alternative to chemical catalysis in response to environmental and social demands for green processes in the pharmaceutical and agrochemical industry. In order to maximize utilization of biocatalytic synthesis, enzymatic properties such as stability, enantioselectivity and substrate spectrum should be suitable for the environments of industrial production. However, design of biocatalytic process is often limited by complicated enzyme properties resulting from biological adaptation, which is incongruous with industrial demands. A representative example is an omega-transaminase which is capable of a stereoselective transfer of an amino group from primary amines to carbonyl compounds without an aid of external cofactors such as NADH. A great deal of research has been made on methods for synthesizing optically pure amines from prochiral ketones using omega-transaminases because optically active amines are very useful as building blocks for a number of drugs and fine chemicals. However, contrary to such industrial demand, omega-transaminases have evolved to use keto-acids as natural amino acceptors rather than ketones, like other kinds of transaminases (e.g., branched-chain amino acid transaminases or aspartate transaminases). All omega-transaminases known to date exhibit marginal activities toward most ketones due to biologically driven substrate specificity. For example, (S)-selective omega-transaminase from *Ochrobactrum anthropi*, (hereinafter, also referred to as "OATA") exhibited low activity toward acetophenone, a representative ketone substrate (i.e., 0.03% relative to pyruvate). In order to compensate for the low reactivity and thereby achieve reasonable reaction rates, a large amount of enzyme should be used. This is a great obstacle for industrial process development.

In order to synthesize optically active amines using omega-transaminases in a practical way, it is necessary to obtain omega-transaminase mutants displaying much higher activity toward ketones. In this regard, Savile et al., proved that substrate specificity could be extended by directed evolution of (R)-selective omega-transaminase from *Arthrobacter* sp. (hereinafter, also referred to as "ARTA") including 27 amino acid substitutions (Science, 2010, 329, 305-309). However, contrary to expectations, the resulting ARTA variant exhibited low activity toward acetophenone (*Advanced Synthesis & Catalysis*, 2015, 357, 1732-1740). In addition, stereoselectivity was considerably damaged for some ketones (i.e., benzylacetone) by the excessive mutations. Accordingly, the present inventors tried to improve enzyme activity for structurally various ketones while not affecting inherent properties such as high stereoselectivity by redesigning active site of omega-transaminase with minimal mutations. For this purpose, OATA was selected because of its high activity toward isopropylamine which is an ideal amino donor for industrial applications. Instead of time-consuming iterative library generation and selection, the present inventors tried to specify key residues that affect ketone reactivity through molecular modeling based on reaction mechanisms and to optimize the corresponding sites by saturated mutagenesis.

Omega-transaminases use pyridoxal 5'-phosphate (PLP) as a prosthetic group to mediate a transfer of an amino group. The overall reaction includes two half-reactions (i.e., oxidative deamination of amino donors and reductive amination of amino acceptors) and involves a series of reaction intermediates such as external aldimine, carbanion intermediate and ketimine. In general, it is considered that carbanion intermediates are the most unstable reaction intermediate, thus resonance-stabilized by a quinonoid structure. Accordingly, it is considerably important to effectively stabilize the quinonoid structure in active sites to achieve high activity of transaminase.

SUMMARY OF THE INVENTION

Therefore, the present invention has been made in view of the above problems, and the objective of the present invention is to provide omega-transaminase mutants with improved activity toward substrates with no reactivity or a very low reaction rate, as compared to a wild-type omega-transaminase.

Another objective of the present invention is to provide a method for producing the omega-transaminase mutants with activity improvement toward ketones.

It is yet another objective of the present invention to provide a method for producing optically active amines using the omega-transaminase mutants.

In accordance with the present invention, the above and other objectives can be accomplished by a point mutation of a wild-type omega-transaminase consisting of the amino acid sequence of SEQ ID NO: 1. The point mutation is rendered by replacing tryptophan at position 58 with the other amino acid.

In accordance with another aspect of the present invention, we provided a method for producing omega-transaminase mutants including construction of an expression vector, transformation of host cells with the recombinant expression vector, and overexpression of the omega-transaminase mutants, followed by purification.

In accordance with another aspect of the present invention, there is provided a method of asymmetric synthesis of an optically active amine by adding the omega-transaminase mutant to a substrate solution comprising an amino donor and a ketone.

In accordance with yet another aspect of the present invention, there is provided a method for producing an optically active amine by kinetic resolution of rac-amines, including addition of the omega-transaminase mutant to a substrate solution comprising an amino acceptor and a racemic amine, and subjecting the racemic amine to selective deamination to obtain an optically active amine.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Asymmetric reductive amination of ketones using omega-transaminase (hereinafter also referred to as "ω-TA") is a promising alternative to synthesis of optically active amines using chemical catalysts. However, the asymmetric reductive amination of ketones using ω-TA has two technical problems: unfavorable reaction equilibrium and very low enzymatic activity toward ketones (for example, less than 1%, as compared to pyruvate). As a result of extensive research to solve the first problem, it was found that equilibrium could be shifted by enzymatic or physicochemical removal of co-products. However, a solution to the second problem has been limited.

The present inventors considered that the inefficient reductive amination of ketones by ω-TA was metabolically relevant to biological needs of microorganisms. Accordingly, the present inventors attempted to increase activity toward ketones by optimizing natural ω-TAs with respect to ketone substrates based on active site redesign.

The present invention relates to ω-TA mutants including a point mutation of a wild-type ω-TA consisting of the amino acid sequence of SEQ ID NO: 1. The point mutation is rendered by replacing tryptophan at position 58 with other amino acids.

The wild-type ω-TA is preferably an ω-TA from *Ochrobactrum anthropic* (hereinafter, also referred to as "OATA WT"), more preferably an ω-TA consisting of the amino acid sequence of SEQ ID NO: 1.

In order to increase amination reaction rates and extend substrate spectrum, active site of wild-type ω-TA consisting of the amino acid sequence of SEQ ID NO: 1 was manipulated by point mutations.

Figure 1:
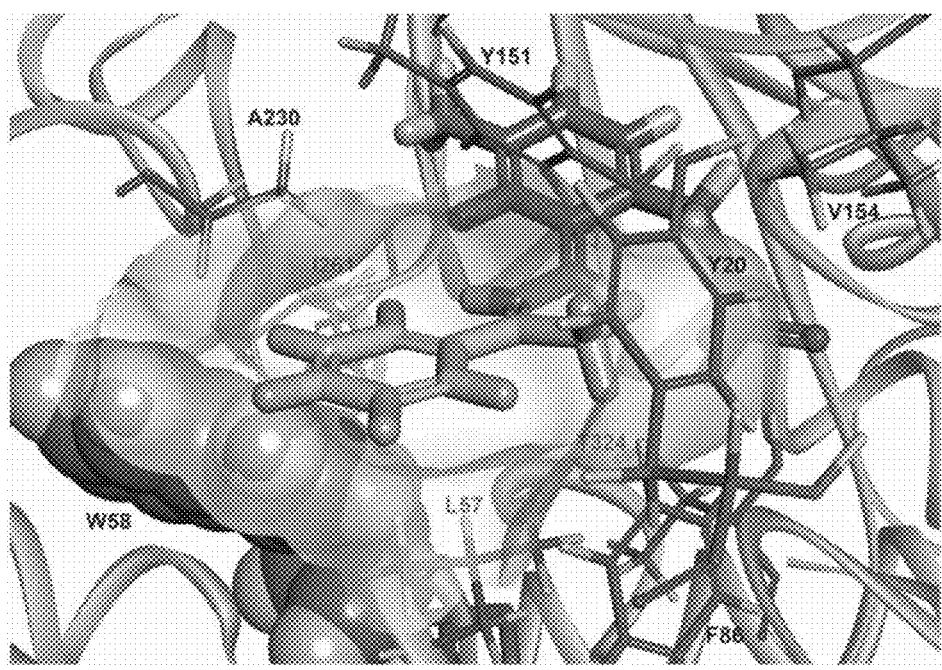
FIG. 1 is an image showing a molecular model of acetophenone-quinonoid intermediate in an active site of a wild-type omega-transaminase from *Ochrobactrum anthropi*. A thick stick represents a quinonoid intermediate where substrate moiety is colored in yellow and thin stick represents active site residues.

The present inventors considered that the wild-type ω-TA exhibited very low activity toward acetophenone compared to natural substrate (i.e., pyruvate) because acetophenone-quinonoid structure was not effectively stabilized. Accordingly, structural differences of molecular environments near quinonoid intermediates were visualized by computer modeling of two quinonoid structures formed with acetophenone and pyruvate. FIG. 1 is an image showing a molecular model of acetophenone-quinonoid intermediate in active site of OATA WT. A thick stick represents a quinonoid intermediate where substrate moiety of quinonoid is colored in yellow and thin stick represents active site residues.

In the molecular model, nine residues including tryptophan at position 58 (hereinafter, also referred to as "W58") were supposed to consist of active site of OATA. Six residues among them (i.e., L57, W58, Y151, A230, I261 and T324) were located within 3-A from a substrate moiety of quinonoid intermediate formed with acetophenone (FIG. 1). Among the nearby residues, W58 was considered to cause considerable steric hindrance with a phenyl substituent of acetophenone. On the other hand, in the case of quinonoid formed with pyruvate, no steric hindrance was observed with the nearby active site residues.

The molecular modeling result predicted that steric hindrance caused by W58 made quinonoid intermediates formed with bulky substrates unstable and led to low activity toward acetophenone. Accordingly, it was expected that replacement of W58 with a sterically less demanding amino acid carrying a smaller side chain could relax steric hindrance of the quinonoid intermediate formed with bulky substrates and thus improve activity.

Figure 2:
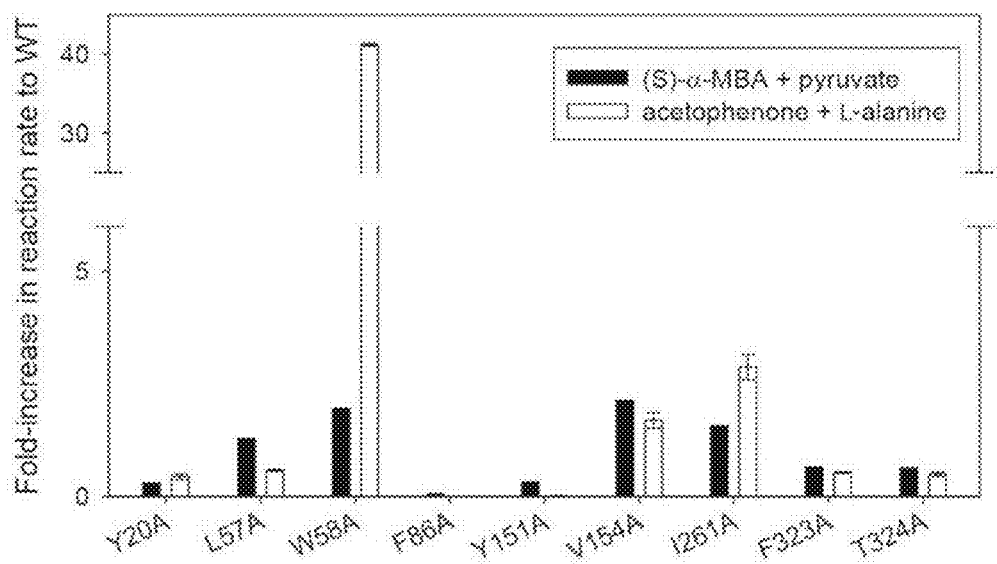
FIG. 2 is a graph showing comparison of reaction rate between omega-transaminase mutants obtained by alanine scanning mutagenesis of active site residues.

In order to verify this, the present inventors performed alanine scanning mutagenesis of eight active site residues except for A230 (FIG. 1) and then examined whether or not the prediction from molecular modeling agreed with an experimental result. Among the resulting alanine scanning mutants, a mutant produced by replacing tryptophan at position 58 with alanine (hereinafter, also referred to as "W58A" or a "W58A mutant") exhibited a greatly increased activity (i.e., 41-fold increase for acetophenone when L-alanine was used as an amino donor). In contrast, mutations elsewhere exhibited no significant activity increase (FIG. 2). The result of acetophenone-quinonoid molecular modeling in the W58A mutant supported the fact that this activity increase resulted from removal of steric hindrance found in wild-type enzymes.

In consideration of the modeling and experimental results, W58 has an important role in steric hindrance of quinonoid intermediate carrying a bulky substituent in the substrate moiety. Thus, W58 was manipulated by partial saturation mutagenesis using hydrophobic residues smaller than tryptophan (i.e., methionine, valine, isoleucine and leucine). Such replacement was also expected to reduce steric hindrance of quinonoid, like replacement of W58A through molecular modeling.

Figure 3:
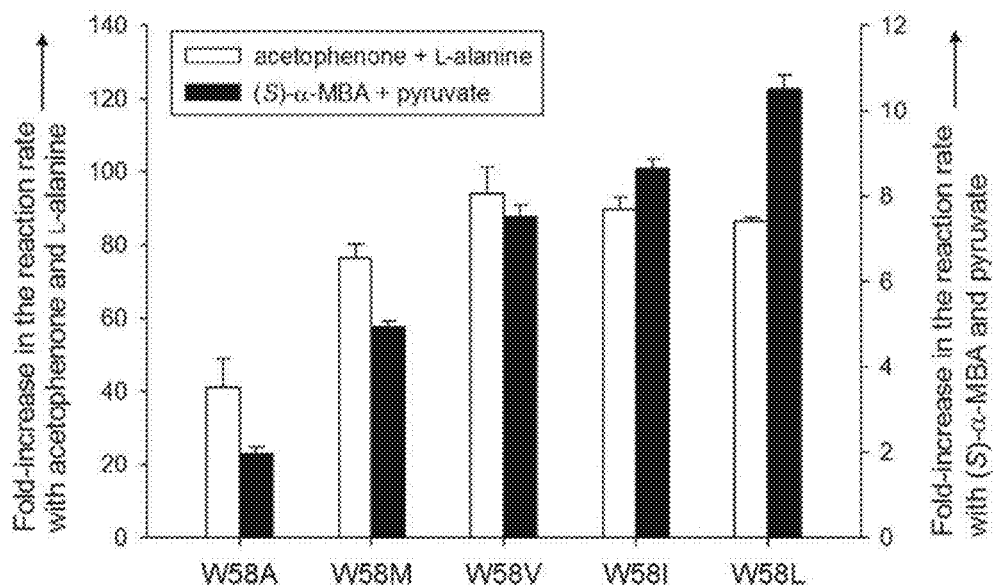
FIG. 3 is a graph showing comparison of reaction rate between a wild-type omega-transaminase and omega-transaminase mutants carrying a W58 point mutation in Example 5 and Example 11.

Replacement with hydrophilic residues was not preferable because indole groups of W58 consisted of hydrophobic patches with side chains of contiguous residues such as M54, L57, V233, I261 and I380. Enzymatic activities of generated mutants including W58A were compared with activities of wild-type enzymes in a reaction using an acetophenone and L-alanine substrate pair and a reaction using a (S)-α-methylbenzylamine (hereinafter, referred to as (S)-α-MBA) and pyruvate substrate pair which is a reverse reaction thereof (FIG. 3). The results showed that there is a positive correlation between enzymatic activities measured with two substrate pairs (Pearson correlation coefficient=0.86). This result means that mutation in W58 has positive effects on both directions of the reversible reaction (i.e. forward and reverse reactions). This is considered because two reactions follow an identical reaction route, but proceed in opposite directions. In addition, all mutations showed the increased ketone amination rate much higher than the forward reaction. This result means that the mutation facilitates amination of acetophenone more selectively than deamination of (S)-α-MBA.

The result of sequence alignment showed that W58, which is a key residue causing steric hindrance regarding amination of ketone, was conserved well in most (S)-selective ω-TAs (Table 1). W58 was perfectly conserved in 11 kinds of ω-TAs among 14 kinds of ω-TAs used for sequence alignment and was replaced with tyrosine acting as a hydrogen bond donor like tryptophan in the remaining 3 kinds of ω-TAs. This means that W58 has a role in strong interaction between carboxylate group of a keto acid substrate and enzyme. From the viewpoint of generating mutants for effective amination of ketones, this results suggest that the present invention is generally applicable to most (S)-selective ω-TAs. The present invention proved that a single point mutation can increase turnover number ($k_{cat}$) of ω-TA for acetophenone up to 20% of $k_{cat}$ of the wild-type enzyme for pyruvate, which demonstrates that low activity of natural ω-TA toward ketone can be improved by rational redesign involving a single point mutation.

TABLE 1

| Bacterial strain | | Amino acid sequence | |
|---|---|---|---|
| Ochrobactrum anthropi | 53 | AMSGLWSVGVG | SEQ ID NO: 31 |
| Pseudomonas putida | 55 | SLSGLWTCGAG | SEQ ID NO: 32 |
| Acinetobacter baumannii | 66 | SLSGLWTCGAG | SEQ ID NO: 33 |
| Acetobacter pasteurianus | 57 | TLSGLWCTPLG | SEQ ID NO: 34 |
| Alcaligenes denitrificans | 48 | GTAGLWCVNAG | SEQ ID NO: 35 |
| Cauiobacter crescentus | 57 | ATSGLWCVNAG | SEQ ID NO: 36 |
| Rhodobacter sphaeroides | 58 | GPAGMWCAQVG | SEQ ID NO: 37 |
| Silicibacter pomeroyl | 58 | AMAGLWCVNIG | SEQ ID NO: 38 |
| Chromobacterium violaceum | 55 | GMAGLWCVNVG | SEQ ID NO: 39 |
| Paracoccus denitrificans | 52 | ANSGLWNMVAG | SEQ ID NO: 40 |
| Vibrio fluvialis | 52 | ANSGLWNMVAG | SEQ ID NO: 41 |

TABLE 1-continued

| Bacterial strain | | Amino acid sequence | |
|---|---|---|---|
| Bacillus megaterium | 55 | FFNQLYCVNLG | SEQ ID NO: 42 |
| mesorhizobium loti | 55 | AFAGLYCVNVG | SEQ ID NO: 43 |
| Silicibacter sp. TM1040 | 54 | AFAGLYCVNVG | SEQ ID NO: 44 |

Accordingly, regarding the omega-transaminase mutants including a point mutation of a wild-type omega-transaminase consisting of the amino acid sequence of SEQ ID NO: 1, the point mutation is rendered by replacing tryptophan at position 58 with the other amino acid of the inherent amino acid of the wild-type omega-transaminase, according to the present invention.

The other amino acid may be preferably a sterically less demanding amino acid than the inherent amino acid of the wild-type omega-transaminase, that is an amino acid with less steric hindrance, more preferably an amino acid having a lower molecular weight than that of the inherent amino acid of the wild-type omega-transaminase, the more preferably a neutral amino acid or an anionic amino acid. The other amino acid may be the more preferably a hydrophobic amino acid or a polar uncharged amino acid, the most preferably a hydrophobic amino acid.

There is no need to particularly limit the hydrophobic amino acid. The hydrophobic amino acid may be any one amino acid selected from the group consisting of alanine, valine, leucine, isoleucine, proline, glycine, phenylalanine and methionine. Preferably, an amino acid having a lower molecular weight than an inherent amino acid of the wild-type omega-transaminase is advantageous in reducing steric hindrance against bulky substrates.

The W58 can be also mutated by polar uncharged amino acids. The polar uncharged amino acid may be any amino acid selected from the group consisting of serine, threonine, cysteine, glutamine, asparagine and tyrosine. Preferably, an amino acid having a lower molecular weight than an inherent amino acid of the wild-type omega-transaminase of OATA is advantageous in reducing steric hindrance with bulky substrates. The polar uncharged amino acid might be disadvantageous in forming hydrophobic patches of active sites, compared to the case of replacement with a hydrophobic amino acid, but is used to control the substrate specificity selectively.

The anionic amino acid may be any one amino acid selected from the group consisting of aspartic acid and glutamic acid. The anionic amino acid might be disadvantageous in forming hydrophobic patches of active sites, compared to the case of replacement with a hydrophobic amino acid, but is used to control the substrate specificity selectively.

In addition, the omega transaminase mutant may contain any amino acid sequence selected from the group consisting of amino acid sequences of SEQ ID NOS: 2 to 17.

In addition to the point mutant in which the tryptophan at position 58 is replaced with the other amino acid, when active site residues at other positions are mutated in combination with the W58 mutation, it was confirmed whether or not amination activities are improved.

Positions at which point mutations are introduced in addition to the point mutation of tryptophan at position 58 are eight active sites such as Y20, L57, F86, Y151, V154, A230, 1261 and T324, excluding, the tryptophan at position 58, among nine active sites of FIG. 1, preferably five active site residues such as L57, Y151, A230, 1261 and T324 which is located within 3-A from the substrate site of quinonoid formed with acetophenone. Alternatively, point mutations may be introduced at neighboring residues such as M54, L57, V233, 1261 and 1380, preferably L57 and 1261, which form hydrophobic patches with indole groups of the tryptophan at position 58.

To confirm this, the present inventors performed alanine scanning mutagenesis and determined whether or not the prediction from molecular modeling was in accordance with the experimental result.

A mutant that includes a point mutation in which tryptophan at position 58 is replaced with alanine and that further includes a point mutation in which leucine at position 57 is replaced with alanine (hereinafter also referred to as "OATA L57A/W58A") exhibited a more 30-fold increase in amination activity, compared to a mutant obtained by replacing tryptophan at position 58 with alanine (hereinafter, also referred to as "OATA W58A") in the reaction using butyrophenone and isopropylamine, and a mutant including a point mutation in which tryptophan at position 58 is replaced with alanine and further including point mutations in which leucine at position 57 is replaced with alanine and valine at position 154 is replaced with alanine (hereinafter, "OATA L57A/W58A/V154A") exhibited an about 93-fold increase in amination activity, compared to OATA W58A.

In addition, toward 2-methyl-1-phenylpropylamine and (S)-α-propylbenzylamine to which the wild-type omega-transaminase (hereinafter, referred to as "OATA WT") exhibited very low activity, OATA L57A/W58A and OATA L57A/W58A/V154A exhibited increases in the deamination activity.

Accordingly, the omega-transaminase mutant of the present invention relates to an omega-transaminase mutant including: a point mutation of a wild-type omega-transaminase consisting of the amino acid sequence of SEQ ID NO: 1; the point mutation is rendered by replacing tryptophan at position 58 with the other amino acid; and a point mutation is rendered by replacing at least one amino acid selected from the group consisting of tyrosine at position 20, methionine at position 54, leucine at position 57, phenylalanine at position 86, tyrosine at position 151, valine at position 154, alanine at position 230, valine at position 233, isoleucine at position 261, threonine at position 324 and isoleucine at position 380, that is, to an omega-transaminase mutant including two or more point mutations. The omega-transaminase mutants, including two or more point mutations, extend a substrate spectrum and thereby increase amination and deamination activity of an omega-transaminase mutant including only one point mutation at position 58.

Regarding the omega-transaminase mutant including two or more point mutations, the other amino acid may be preferably a sterically less demanding amino acid than the inherent amino acid of the wild-type omega-transaminase, that is an amino acid with less steric hindrance, more preferably an amino acid having a lower molecular weight than that of the inherent amino acid of the wild-type omega-transaminase, the more preferably a neutral amino acid or an anionic amino acid. The other amino acid may be the more preferably a hydrophobic amino acid or a polar uncharged amino acid, the most preferably a hydrophobic amino acid.

In addition, the omega transaminase mutant may contain any amino acid sequence selected from the group consisting of amino acid sequences of SEQ ID NOS: 18 to 30.

In addition, the present invention provides a method to generate an omega-transaminase mutant including recombining genes coding the omega-transaminase mutant with an expression vector, transforming host cells with the recombinant expression vector, and expressing the omega-transaminase mutant, followed by purification.

In addition, the present invention provides a method for asymmetric synthesis of an optically active amine by adding the omega-transaminase mutant to a substrate solution including an amino donor and a ketone.

In addition, the present invention provides a method for producing an optically active amine by kinetic resolution of rac-amine, including adding the omega-transaminase mutant to a substrate solution comprising an amino acceptor and a racemic amine, and subjecting the racemic amine to selective deamination to obtain an optically active amine.

Example 1: Construction of Recombinant Vector of Wild-Type Omega-Transaminase

*Ochrobactrum anthropi* was cultured in LB medium (or broth) (tryptone 10 g/L, yeast extract 5 g/L, sodium chloride 10 g/L, pH 7) at 37° C. for 12 hours, and gene encoding OATA WT was obtained by PCR amplification using oligonucleotide primers. The amplified gene was ligated into an expression vector pET28a(+), using Nco1 and Eag1 restriction enzymes and a ligase. Primers used herein are shown in the following Table 2.

TABLE 2

| Primer | Base sequence | |
|---|---|---|
| Forward primer | 5'-GATATACCATGGNNACTGCTCAGCC AAACTCT-3' | SEQ ID NO: 45 |
| Reverse primer | 5'-CGAGTGCGGCCGTCCTGGTGAGGCT TGC-3' | SEQ ID NO: 46 |

Example 2: Construction of Recombinant Vector for Expressing Omega-Transaminase Mutants Carrying Point Mutation at Position 58

Site-directed mutagenesis was performed to introduce mutation at position 58. The recombinant vectors for expression of omega-transaminase carrying point mutation at position 58 were obtained by PCR amplification using oligonucleotide primers and the plasmid obtained in Example 1. The amplified plasmids were treated with Dpn1 restriction enzyme and *Escherichia coli* XL10-Gold was transformed with the plasmid. The transformed *E. coli* XL10-Gold was cultured in a kanamycin-containing LB-agar medium (tryptone 10 g/L, yeast extract 5 g/L, sodium chloride 10 g/L, agar 15 g/L, pH 7) at 37° C. for 15 hours. Each colony was cultured in a kanamycin-containing LB-broth at 37° C. for 15 hours and the plasmids were extracted from each cells. The mutation was identified by DNA sequencing. Primers used herein are shown in the following Table 3.

TABLE 3

| Primer | Base sequence | |
|---|---|---|
| Forward primer | 5'-CGAAGCGATGTCAGGACTGVTKAG TGTTGGCGTGGGCTTTT-3' | SEQ ID NO: 47 |
| Reverse primer | 5'-AAAAGCCCACGCCAACACTMABCA GTCCTGACATCGCTTCG-3' | SEQ ID NO: 48 |

Example 3: Construction of Recombinant Vector for Expressing Omega-Transaminase Carrying Point Mutations at Multiple Positions Including Position 58

Site-directed mutagenesis was performed to introduce mutations at multi sites. The recombinant vectors for expression of omega-transaminase carrying point mutations at multiple positions including position 58 were obtained by PCR amplification using a DNA primer and the plasmid obtained in Example 1. The amplified plasmids were treated with Dpn1 restriction enzyme and *E. coli* XL10-Gold was transformed with the plasmid. The transformed *E. coli* XL10-Gold was cultured in a kanamycin-containing LB-agar medium (tryptone 10 g/L, yeast extract 5 g/L, sodium chloride 10 g/L, agar 15 g/L, pH 7) at 37° C. for 15 hours. Each colony was cultured in a kanamycin-containing LB-broth at 37° C. for 15 hours and the plasmid was extracted. The mutation was identified by DNA sequencing. Primers used herein are shown in the following Table 4.

TABLE 4

| Mutants | Base sequence | |
|---|---|---|
| L57A/W58A | 5'-CGAAGCGATGTCAGGAG CGTGGAGTGTTGGCGTG-3' | SEQ ID NO: 49 |
| | 5'-CGATGTCAGGAGCGGCG AGTGTTGGCGTGGG-3' | SEQ ID NO: 50 |
| L57A/W58A/V154A | 5'-CGAAGCGATGTCAGGAG CGTGGAGTGTTGGCGTG-3' | SEQ ID NO: 51 |
| | 5'-CGATGTCAGGAGCGGCG AGTGTTGGCGTGGG-3' | SEQ ID NO: 52 |
| | 5'-CGGCTATCACGGTGCGA CGATTGCCTCTG-3' | SEQ ID NO: 53 |
| W58D/I261A L57Q/W58N/I261L L57C/W58L/I261A | 5'-AAGCGCTATATCGAAGC GATGTCAGGANNNNNNAGTG TTGGCGTGGGCTTTTCCGAAC-3' | SEQ ID NO: 54 |
| | 5'-TCTGCTGATCGCCGACG AGGTTNNNTGCGGCTTCGGA-3' | SEQ ID NO: 55 |

Example 4: Overexpression and Purification of Omega-Transaminases

*E. coli* BL21 (DE3) was transformed with the recombinant vectors obtained in Examples 1 to 3. The transformed *Escherichia coli* BL21 (DE3) was cultured in 1 L of a kanamycin-containing (50 μg/mL) LB-broth and IPTG (final concentration: 0.1 mM) was added when an optical density (OD) reached 0.4. Then, the resulting transformed *Escherichia coli* BL21 (DE3) was cultured at 37° C. for more than 6 hours and centrifuged at 10,000×g at 4° C. for 20 minutes to obtain bacterial cells. The bacterial cells were resuspended in 15 mL of a resuspension buffer (50 mM Tris-HCl, 50 mM sodium chloride, 1 mM EDTA, 0.02% sodium azide, 1 mM B mercaptoethanol, 0.1 mM PMSF, 0.5 mM PLP, pH 7). The cell suspension was disrupted by ultrasonicator while cooled in an ice bath, and centrifuged at 17,000×g and 4° C. for 30 minutes to remove cell debris. OATA WT, and omega-transaminase mutants (OATA W58A, W58V, W58L, W58I, W58M, L57A/W58A, L57A/W58A/V154A, W58D/I261A, L57C/W58L/I126A and L57Q/W58N/I121L) were respectively purified using AKTAprime plus (GE Healthcare, Piscataway, USA). The crude extract was loaded on a HisTrap HP column (GE Healthcare) and eluted with a gradient of imidazole (0.05-0.5 M) in the buffer (20 mM sodium phosphate, 0.5 M sodium chloride, 0.5 mM PLP, pH 7.4). Residual imidazole was removed by loading on a HiTrap desalting column (Ge Healthcare) with the buffer (50 mM sodium phosphate, 0.15 M sodium chloride, 0.5 mM PLP, pH 7).

Example 5: Activity of Omega-Transaminase Carrying W58 Point Mutation Toward Various Ketones In order to evaluate availability of synthesis using OATA carrying W58 point mutation, the present inventors investigated activities toward structurally diverse ketones using isopropylamine as an amino donor and results are shown in the following Table 5.

TABLE 5

$$R_1\text{-CO-}R_2 \text{ (1a-o)} + \text{iPr-NH}_2 \text{ (2)} \rightarrow R_1\text{-CH(NH}_2\text{)-}R_2 \text{ (3a-o)} + \text{acetone}$$

| | Substituents | | Reaction rate (μm/h) | | Fold-increase |
|---|---|---|---|---|---|
| Ketones | $R_1$ | $R_2$ | OATA | OATA$_{WSBL}$ | |
| 1a | —$C_6H_5$ | —$CH_3$ | 1.92 ± 0.02 | 316 ± 10 | 165 |
| 1b | —$C_6H_5$ | —$CH_2CH_3$ | 0.02 ± 0.01 | 5.2 ± 0.2 | 260 |
| 1c | —$C_6H_5$ | —$(CH_2)_2CH_3$ | n.d. | 0.13 ± 0.01 | >130 |
| 1d | —$C_6H_5$-p-$CH_3$ | —$CH_3$ | 0.97 ± 0.02 | 162 ± 8 | 167 |
| 1e | —$C_6H_5$-p-$OCH_3$ | —$CH_3$ | 0.55 ± 0.01 | 110 ± 2 | 200 |
| 1f | —$(CH_2)_2C_6H_5$ | —$CH_3$ | 10.3 ± 0.1 | 885 ± 5 | 86 |
| 1g | indanone | | n.d. | 7.6 ± 0.1 | >760 |
| 1h | tetralone | | n.d. | 2.1 ± 0.1 | >210 |
| 1i | 1-naphthyl | —$CH_3$ | 0.82 ± 0.02 | 150 ± 10 | 183 |
| 1j | —$(CH_2)_2CH_3$ | —$CH_3$ | 1.6 ± 0.1 | 445 ± 15 | 278 |
| 1k | —$(CH_2)_3CH_3$ | —$CH_3$ | 2.9 ± 0.1 | 895 ± 40 | 309 |
| 1l | —$(CH_2)_3CH_3$ | —$CH_3$ | 4.0 ± 0.2 | 670 ± 30 | 167 |
| 1m | —$CH(CH_3)_2$ | —$CH_3$ | 3.1 ± 0.1 | 250 ± 55 | 81 |
| 1n | —$CH_2CH(CH_3)_2$ | —$CH_3$ | 0.40 ± 0.01 | 195 ± 5 | 487 |
| 1o | cyclopropyl | —$CH_3$ | 0.32 ± 0.01 | 13.0 ± 0.1 | 41 |

OATA W58L exhibited a remarkable increase in activity, that is, a 41- to 760-fold increase in reaction rate, with respect to all tested ketones (9 kinds of arylalkyl ketones 1a to 1i and 6 kinds of alkyl ketones 1j to 1o). Considerable activity improvement was observed for ketones 1c and 1g, 1h that did not react with OATA WT.

Unlike ARTA manipulated by Savile et al (hereinafter, also referred to as "ARTAmut" (Science, 2010, 329, 305-309) by which ee of (S)-1-methyl-3-phenylpropylamine synthesized is 68%(*Advanced Synthesis & Catalysis*, 2015, 357, 1732-1740), enantiopure amines were synthesized by the OATA W58L from all ketones (>99% ee). Also, OATA W58L exhibited effective amination of bulky ketones having naphthyl (1i) and n-hexyl (1l) substituents.

In order to determine whether or not OATA W58A, OATA W58M, OATA W58V and OATA W58I mutants exhibit the activity increase toward ketones, enzyme reaction was performed in 10 mM acetophenone and 10 mM L-alanine. The result showed that all of these mutants exhibited more than 40-fold increase in reactivity as compared to the OATA WT, as shown in FIG. 3.

In addition, in order to evaluate availability of synthesis of optically pure amines using the omega-transaminase mutant with a W58 point mutation, substrate specificity to various ketones was measured by enzymatic assay using aldehyde dehydrogenase. The omega transaminase mutants purified in Example 4 and an aldehyde dehydrogenase were subjected to reaction under the following conditions: 50 mM benzylamine, 5 mM ketone, 2 mM NAD+10% DMSO, 50 mM TrisCl buffer pH 7, 37° C., the produced NADH was measured at 340 nm by microplate spectrophotometer PowerWave X 340 (Biotek, USA) and results are shown in the following Table 6.

ficity toward ketones and in was considered that optically active amines could be synthesized from various ketones using any one of W58 point-mutated omega-transaminase mutants.

Example 6: Activity of Omega-Transaminase Mutants Carrying Point Mutations at Multiple Positions Including Position 58 Toward Various Ketones In order to evaluate availability of synthesis of optically pure amines using the omega-transaminase mutant carrying point mutations at multiple positions including position 58, substrate specificity to various ketones was measured. The omega transaminase mutants purified in Example 4 was added under the following conditions: 500 mM isopropylamine (in the case of OATA W58D/I261A, L-alanine was used; and in the case of OATA L57Q/W58N/I261L and OATA L57C/W58L/I261A, benzylamine was used), 50 mM ketone, 15% DMSO, 50 mM phosphate buffer pH 7 and 37°

TABLE 6

| Ketones | Relative activity to acetophenone | | | | | |
|---|---|---|---|---|---|---|
| | OATA WT | OATA W58A | OATA W58V | OATA W58I | OATA W58L | OATA W58M |
| acetophenone | 100% | 100% | 100% | 100% | 100% | 100% |
| propiophenone | 1% | 14% | 16% | 14% | 2% | 17% |
| butyrophenone | 0% | 8% | 12% | 11% | >0.1% | 15% |
| 4-methylacetophenone | 51% | 56% | 52% | 74% | 51% | 68% |
| 4-methoxyacetophenone | 29% | 30% | 30% | 38% | 34% | 42% |
| 1-indanone | n.d. | 15% | 17% | 16% | 2% | 20% |
| α-tetralone | n.d. | 19% | 12% | 16% | 0.7% | 17% |
| benzylacetone | 536% | 219% | 193% | 125% | 277% | 178% |
| 1-acetonaphthone | 43% | | | | 47% | |
| 2-hydroxyacetophenone | | 61% | 70% | 73% | | 65% |
| 2-butanone | 317% | 16% | 17% | 20% | 78% | 25% |
| 2-pentanone | 83% | 15% | 28% | 21% | 141% | 25% |
| 2-hexanone | 151% | 52% | 62% | 54% | 281% | 57% |
| 2-octanone | 208% | 122% | 140% | 73% | 209% | 81% |
| hydroxyacetone | 364% | 31% | 32% | 42% | 23% | 44% |
| methoxyacetone | 571% | 135% | 152% | 166% | 424% | 159% |
| 3-methyl 2-butanone | 161% | 21% | 29% | 26% | 78% | 29% |
| 1-hydroxy-2-butanone | | 9% | 8% | 16% | | 21% |
| 3-hydroxy-2-butanone | | 20% | 29% | 23% | | 32% |
| 4-hydroxy-2-butanone | | 17% | 20% | 20% | | 29% |
| 4-methyl-2-pentanone | 21% | 46% | 35% | 41% | 61% | 38% |
| cyclopropyl methyl ketone | 17% | 14% | 14% | 17% | 4% | 19% |
| acetone | | 19% | 18% | 18% | | 19% |

4 kinds of omega-transaminase mutants (i.e., W58A, W58V, W58I and W58M) exhibited similar substrate speci- C., and subjected to reaction, and results are shown in the following Table 7.

TABLE 7

| Ketones | Relative activity | | | | | | | |
|---|---|---|---|---|---|---|---|---|
| | OATA WT | OATA L57A | OATA W58A | OATA L57A/ W58A | OATA L57A/W58A/ V154A | OATA W58D/ I261A | OATA L57Q/W58N/ I261L | OATA L57C/W58L/ I261A |
| acetophenone | 100% | 89% | 1,206% | 716% | 637% | 648% | 2,500% | 12,174% |
| propiophenone | 17% | 49% | 259% | 387% | 821% | | | n.d. |
| butyrophenone | 2% | 1% | 8% | 302% | 747% | | | n.d. |

TABLE 7-continued

| Ketones | OATA WT | OATA L57A | OATA W58A | OATA L57A/ W58A | OATA L57A/W58A/ V154A | OATA W58D/ I261A | OATA L57Q/W58N/ I261L | OATA L57C/W58L/ I261A |
|---|---|---|---|---|---|---|---|---|
| 4-methylacetophenone | | | | | | | | 1,096% |
| 4-methoxyacetophenone | | | | | | | | 4,017% |
| 1-indanone | | 0.6% | | | | | | 609% |
| α-tetralone | | n.d. | | | | | | 243% |
| benzylacetone | | 439% | | | | | | 6,330% |
| 2-butanone | | | | | | | | n.d. |
| 2-pentanone | | | | | | | | n.d. |
| 2-hexanone | | | | | | | | n.d. |
| 2-octanone | | | | | | | | 13,757% |
| 3-methyl 2-butanone | | | | | | | | n.d. |
| 1-hydroxy-2-butanone | | | | | | | | n.d. |
| 3-hydroxy-2-butanone | | | | | | | | n.d. |
| 4-hydroxy-2-butanone | | | | | | | | n.d. |
| 4-methyl-2-pentanone | | | | | | | | n.d. |
| cyclpropyl methyl ketone | | | | | | | | n.d. |
| acetone | | | | | | | | n.d. |

Like the omega-transaminase mutants carrying W58 point mutation, the omega-transaminase mutants carrying point mutations at multiple positions exhibited a great increase in activity toward ketones, in particular, OATA L57A/W58A and OATA L57A/W58A/V154A exhibited a remarkable increase in activity for butyrophenone (i.e., a 38- and 93-fold increase respectively) compared with OATA W58A. Because OATA L57A exhibited low activity toward ketones, like OATA WT, it was considered that the increased amination activity of OATA L57A/W58A and OATA L57A/W58A/V154A resulted from the W58 point mutation.

OATA L57C/W58L/I261A selectively catalyzed ketones depending on their structures, that is, no amination activity was observed toward alkyl ketone excluding 2-octanone, but a great increase in amination activity toward arylalkyl ketone, as compared to OATA WT, like OATA W58L.

OATA W58D/I261A in which tryptophan at position 58 is modified with a hydrophilic amino acid exhibited a 6-fold increase in amination activity toward ketone than OATA WT, despite of a smaller increment than other mutants in which modified with a hydrophobic amino acid.

Example 7: Kinetic Analysis of OATA W58L According to Substrates

In order to find the mechanism by which OATA W58L increases activity, kinetic analysis was performed using 4 kinds of representative substrates. Analysis conditions and results are shown in Table 8 and Table 9, respectively.

TABLE 8

| Enzyme | Substrate | Concentration range of substrate (mM) | Cosubstrate | Concentration of cosubstrate (mM) | HPLC analyte |
|---|---|---|---|---|---|
| OATA | acetophenone | 10-140 | isopropylamine | 100 | (S)-α-MBA |
| OATA | pyruvate | 0.05-0.5 | (S)-α-MBA | 10 | acetophenone |
| OATA | (S)-α-MBA | 30-250 | pyruvate | 10 | acetophenone |
| OATA | isopropylamine | 50-800 | pyruvate | 10 | L-alanine |
| OATA$_{W58L}$ | acetophenone | 5-100 | isopropylamine | 100 | (S)-α-MBA |
| OATA$_{W58L}$ | pyruvate | 0.5-10 | (S)-α-MBA | 10 | acetophenone |
| OATA$_{W58L}$ | (S)-α-MBA | 0.2-2.5 | pyruvate | 10 | acetophenone |
| OATA$_{W58L}$ | isopropylamine | 1-160 | pyruvate | 10 | L-alanine |

TABLE 9

| | Rate constants (OATA, OATA$_{W58L}$) | | | Fold- |
|---|---|---|---|---|
| Substrate | $K_M$ (mM) | $k_{cat}$ ($\times 10^{-3} s^{-1}$) | $k_{cat}/K_M$ ($M^{-1} s^{-1}$) | increase in $k_{cat}/K_M$ |
| acetophenone | 110, 18 | 9.7, 540 | 0.088, 30 | 340 |
| pyruvate | 0.12, 2.1 | 2600, 19000 | 22000, 9000 | 0.41 |
| (S)-α-MBA | 150, 0.73 | 24000, 20000 | 160, 27000 | 170 |
| isopropylamine | 470, 53 | 9700, 9300 | 21, 180 | 8.6 |

Like the modeling result, OATA W58L exhibited a 55.7-fold increase in turnover number ($k_{cat}$) to acetophenone. Also, the formation of Michaelis complexes was facilitated by W58L substitution (i.e., 6.1-fold tighter binding). This was considered as binding of acetophenone to active sites is hindered by W58. In actual, the result of docking simulation showed that there is considerable steric hindrance between W58 and the phenyl substituent of acetophenone in the Michaelis complex. The facilitated binding and increased turnover resulted in a 340-fold increase in specificity constant ($k_{cat}/K_M$) of OATA W58L for acetophenone.

Unlike acetophenone, OATA W58L showed weaker binding to pyruvate (17.5-fold decrease in $K_M$) compared to OATA WT. This is considered as potential hydrogen bond donor (i.e., indole group of W58) was lost by W58L substitution, thus the interaction between pyruvate and carboxylate is weakened. However, catalytic turnover of pyruvate was faster in OATA W58L than OATA WT (i.e., 7.1-fold increase in $k_{cat}$).

The increases in $k_{cat}$ for both acetophenone and pyruvate mean that acceleration of catalytic turnover caused by W58L substitution is irrelevant to hydrophobicity of substrates. In spite of increased catalytic turnover, specificity constant ($k_{cat}/K_M$) for pyruvate was decreased by 60% due to a decrease in the binding affinity by W58L substitution. The facilitated binding of OATA W58L to the hydrophobic substrate (i.e., acetophenone) was further remarkable in the case of (S)-α-MBA (207-fold decrease in $K_M$).

On the contrary to expectation, OATA W58L exhibited stronger binding to isopropylamine (8.9-fold decrease in $K_M$). This result means that a substrate having even a methyl substituent is hindered by W58. On the contrary to the increase in $k_{cat}$ for amino acceptors, catalytic turnover number was not greatly changed for amino donors (i.e., (S)-α-MBA and isopropylamine) by W58 substitution. This result means that W58L mutation selectively promotes the amination reaction over deamination reaction. Owing to great increase in $k_{cat}/K_M$ for acetophenone as well as 8.6-fold increase in $k_{cat}/K_M$ for isopropylamine, OATA W58L is suitable for large scale processes using isopropylamine as an amino donor of which deamination product (i.e., acetone) is easily removed at the reduced pressure by overcoming the unfavorable thermodynamic equilibrium.

Figure 4:
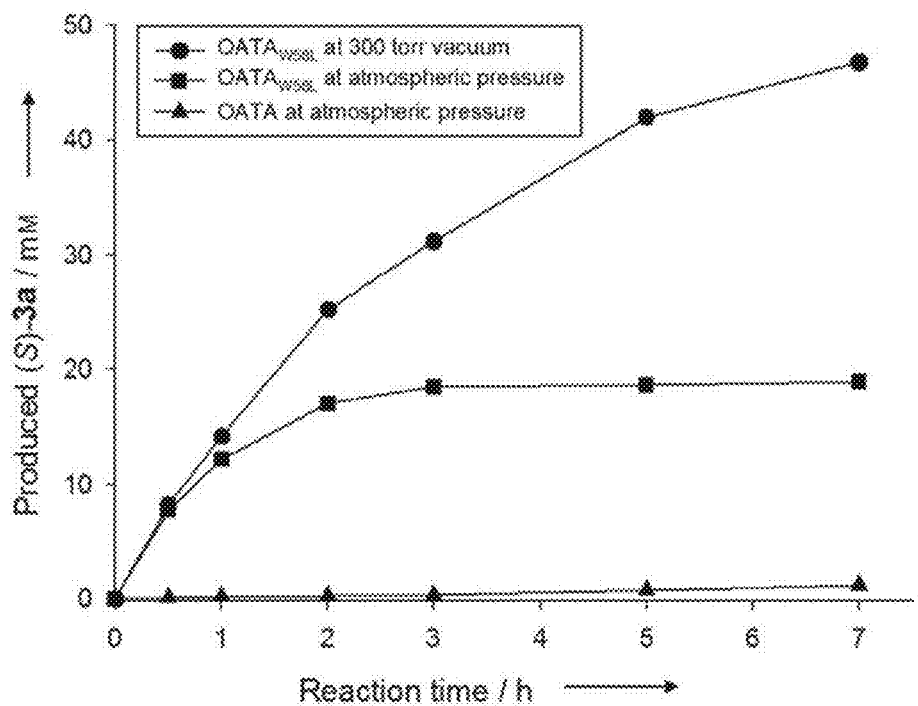
FIG. 4 is a graph showing results of asymmetric synthesis of (S)-α-methylbenzylamine using the omega-transaminase mutant with W58L substitution and the wild-type omega-transaminase in Example 9.

Example 8: Asymmetric Synthesis of (S)-α-MBA Using Omega-Transaminase Mutant with W58L Substitution In order to confirm OATA W58L is suitable for asymmetric synthesis of chiral amines, OATA WT or OATA W58L was added under the following conditions: acetophenone (50 mM), isopropylamine (500 mM), PLP (0.1 mM), phosphate buffer (50 mM, pH 7) and DMSO (15% v/v). Produced (S)-α-MBA was monitored with time at 37° C. and atmospheric pressure (FIG. 4).

Figure 5:
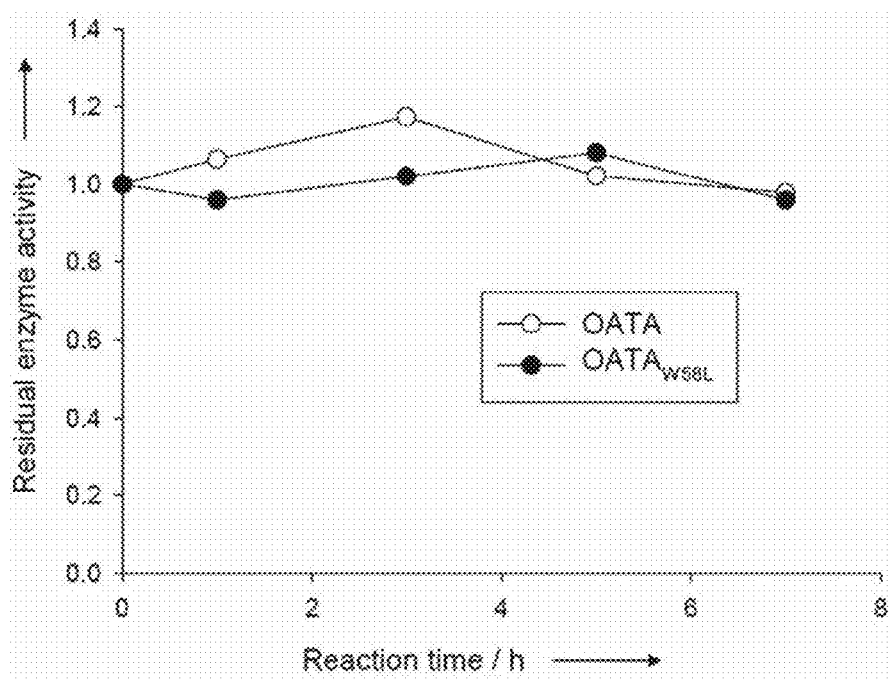
FIG. 5 is a graph showing comparison of enzyme stability between the wild-type omega-transaminase and the omega-transaminase mutant with W58L substitution in Example 9.

As expected, amination of acetophenone occurred efficiently without loss of stereoselectivity (ee of produced (S)-α-MBA>99%). Neither OATA WT nor OATA W58L exhibited activity loss over the overall reaction, which means that W58L mutation did not affect the stability of enzymes (FIG. 5). On the other hand, ARTAmut exhibited a considerable decrease in enzyme stability, as compared to the wild-type ARTA (*Advanced Synthesis & Catalysis*, 2015, 357, 1732-1740). Conversion did not rise further than 37% on asymmetric synthesis of (S)-α-MBA using OATA W58L at atmospheric pressure i.e., only 1% increase in conversion from 3 hours to 7 hours) despite its high stability (FIG. 4). This is considered as reaction equilibrium is unfavorable. Based on the precedent research, the concentration of (S)-α-MBA would not exceed 25.9 mM under given reaction conditions because the equilibrium constant of acetophenone/isopropylamine reaction in the absence of DMSO was calculated as $5.86 \times 10^{-2}$. In actual, a conversion reached 94% in 7 hours using OATA W58L when acetone was removed under a vacuum of 300 torr. On the other hand, ARTAmut exhibited only a conversion of 19% in 7 hours under the same reaction conditions (*Advanced Synthesis & Catalysis*, 2015, 357, 1732-1740).

Example 9: Asymmetric Synthesis of Chiral Amines Using Omega-Transaminase Mutant with W58L Substitution In addition, in order to evaluate availability of synthesis of optically pure amines using OATA W58L, asymmetric synthesis of amines was performed using 5 kinds of ketones. 5 mg/mL OATA WT or OATA W58L purified in Example 4 was added under the following conditions: 50 mM ketone, 500 mM isopropylamine, 0.1 mM PLP, 50 mM phosphate buffer pH 7, 15% (v/v) DMSO, vacuum of 300 torr and 37° C., amounts of chiral amines produced were measured according time and enantiomeric excess (ee) thereof was calculated. As a result, optically pure (S)-amines (>99% ee) were obtained. Results are shown in the following Table 10.

TABLE 10

| Substrate | Reaction time (h) | Conversion (%) OATA | Conversion (%) OATA$_{W58L}$ | Product (% ees) |
|---|---|---|---|---|
| 4-methylacetophenone | 7 | 7 | 91 | (S)-α,4-dimethylbenzylamine (>99) |
| benzylacetone | 5 | 26 | 93 | (S)-1-methyl-3-phenylpropylamine (>99) |
| 1-acetonaphthone | 15 | 13 | 75 | (S)-1-(1-naphthyl)ethylamine (>99) |
| 2-hexanone | 10 | 14 | 93 | (S)-2-aminohexane (>99) |
| 2-octanone | 15 | 30 | 91 | (S)-2-aminooctane (>99) |

As compared to the case of OATA WT, OATA W58L afforded much higher conversion (over 90% within 15 hours except for 1-acetonaphthone). One of these ketones (i.e., benzylacetone) was subjected to synthesis with a preparative scale under vacuum of 300 torr in 100 mL of a reaction mixture containing benzylacetone (1.5 g, 10 mmol), isopropylamine (8.6 mL, 100 mmol), OATA W58L (5 µmol), DMSO (15 mL) and phosphate buffer (50 mM, pH 7). Conversion reached 92% in 18 hours and ee of (S)-1-methyl-3-phenylpropylamine (hereinafter, referred to as "(S)-1-M-3-PPA") was over 99%. At this time, protein was precipitated at pH adjusted to 1.0 by addition of 5 N HCl into the reaction mixture and the mixture was filtered through a glass-frit filter funnel to remove the protein precipitate. The filtrate was loaded on a glass column filled with a Dowex 50WX8 cation-exchange resin (40 g) and the column was washed with water (200 mL) and then eluted with 150 mL of a 10% ammonia solution. 1.22 g (yield 81.3%, >99% ee) of (S)-1-M-3-PPA was obtained by evaporation of collected elution fractions at 50° C. and 0.25 bar. Purity was identified by structural analysis.

Example 10: Production of Amines by Kinetic Resolution Using Omega-Transaminase Mutants Including W58 Point Mutation In order to produce optically pure amines by kinetic resolution using the omega-transaminase mutant, substrate specificity for various amines was measured.

OATA WT, OATA W58A or OATA W58L purified in Example 4 was added under the following conditions: 50 mM (S)-amine (or 100 mM racemic amine), 50 mM pyruvate, 50 mM phosphate buffer pH 7 and 37° C. Reaction was performed for 10 minutes and results are shown in the following Table 11.

TABLE 11

| Amines | Relative reactivity | | |
|---|---|---|---|
| | OATA | OATA W58A | OATA W58L |
| (S)-α-methylbenzylamine | 100% | 100% | 100% |
| (S)-α-ethylbenzylamine | 2% | 44% | 20% |
| (S)-α-propylbenzylamine | 0.2% | 10% | 2% |
| 1-Methyl-3-phenylpropylamine | 73% | 151% | 202% |
| 2-Methyl-1-phenylpropan-1-amine | 0.1% | 3% | 2% |
| 2,2-Dimethyl-1-phenylpropan-1-amine | 0.1% | 3% | 2% |
| 4-Fluoro-α-methylbenzylamine | 31% | 117% | 283% |
| (S)-4-methoxy-α-methylbenzylamine | 116% | 44% | 98% |
| (S)-α,4-dimethylbenzylamine | 86% | 45% | 78% |
| Benzylamine | 274% | 50% | 49% |
| Mexiletine | 27% | 197% | 284% |
| (S)-1-aminoindan | 9% | 100% | 54% |
| (S)-1,2,3,4-Tetrahydro-1-naphthylamine | 2% | 69% | 17% |
| (S)-1-(1-naphthyl)ethylamine | 0.5% | 0.7% | 2% |
| Isopropylamine | 20% | 28% | 72% |
| (S)-sec-butylamine | 29% | 66% | 266% |
| 2-Aminopentane | 13% | 194% | 272% |
| (S)-2-aminohexane | 31% | 116% | 306% |
| (S)-2-aminooctane | 146% | 99% | 255% |
| 1,3-Dimethylbutylamine | 3% | 173% | 283% |
| 1,2-Dimethylpropylamine | 18% | 101% | 305% |
| (S)-1-Cyclopropylethylamine | 29% | 79% | 233% |
| 1-Methoxy-2-propylamine | 29% | 126% | 119% |
| DL-Alaninol | 16% | 13% | 39% |

The omega-transaminase mutants with a W58 point mutation exhibited a different substrate specificity to amine, as compared to OATA WT, in particular, exhibited a great increase in reactivity toward (S)-1,2,3,4-tetrahydro-1-naphthylamine and 1,3-dimethylbutylamine to which OATA WT exhibited low reactivity.

In order to confirm whether or not OATA W58A, OATA W58M, OATA W58V and OATA W58I mutants, in addition to the OATA W58L mutant, exhibit activity increase toward amine, these mutants were reacted with 10 mM (S)-α-methylbenzylamine and 10 mM pyruvate. As a result, 2- to 10-fold improvement was observed in the deamination activity than OATA WT, as shown in FIG. 3.

Also, omega transaminase carrying point mutations at multiple positions purified in Example 4 was reacted under the following conditions: 10 mM (S)-amine (or 20 mM racemic amine), 10 mM pyruvate, 50 mM phosphate buffer pH 7 and 37° C. Results are shown in the following Table 12.

TABLE 12

| Amines | Relative activity | | | | | |
|---|---|---|---|---|---|---|
| | OATA WT | OATA L57A/ W58A | OATA L57A/W58A/ V154A | OATA W58D/ I261A | OATA L57Q/W58N/ I261L | OATA L57C/W58L/ I261A |
| (S)-α-methylbenzylamine | 100% | 621% | 1,190% | 17% | 262% | 900% |
| (S)-α-ethylbenzylamine | | 202% | 707% | | | |
| (S)-α-propylbenzylamine | | 240% | 749% | | | |
| (S)-1,2,3,4-tetrahydro-1-naphtylamine | | 209% | 625% | | | |
| (S)-1-(1-naphtylethylamine | | 18% | 60% | | | |
| rac-2-methyl-1-phenylpropylamine | | 12% | 167% | | | |
| benzylamine | | | | 17% | 123% | 792% |
| isopropylamine | | | | n.d. | 23% | 8% |

In the case of the omega transaminase carrying point mutations at multiple positions, substrate specificity toward amines was also changed, like the W58 point mutant, in particular, OATA L57A/W58A and OATA L57A/W58A/V154A, including W58A point mutation, exhibited a great increase in activity toward (S)-α-propylbenzylamine and rac-2-methyl-1-phenylpropylamine to which OATA W58A exhibited low activity (i.e., 20% and 6% relative activity to (S)-α-MBA measured with OATA WT, respectively).

OATA L57C/W58L/I261A exhibited a decrease in activity toward isopropylamine, but a great increase in activity toward arylalkylamine such as (S)-α-MBA and benzylamine (i.e., 900% and 792% relative activity to (S)-α-MBA measured with OATA WT, respectively), like OATA W58L, as compared to OATA WT.

OATA W58D/I261A in which tryptophan at position 58 was modified with a hydrophilic amino acid exhibited a great decrease in activity toward amines (i.e., 17% relative activity for (S)-α-MBA to (S)-α-MBA measured with OATA WT).

Based on these results, kinetic resolution of rac-amines was attempted to prepare optically pure amines using OATA W58L.

2 mg/mL of OATA W58L was added under the following conditions: 100 mM racemic amine, 100 mM pyruvate, 0.1 mM PLP, 50 mM phosphate buffer pH 7, and 37° C. Amount of amines was measured with time and enantiomeric excess (ee) thereof was calculated.

As a result, when OATA W58L was added, an optically pure (R)-amine was obtained (>99% ee). Results are shown in Table 13.

TABLE 13

| Amines | Reaction time (h) | Product (% $ee_R$) | |
|---|---|---|---|
| | | OATA | OATA$_{W58L}$ |
| rac-1-amino | 0.5 | 4.6 | >99 |
| rac-1,2,3,4-tetrahydro-1-naphthylamine | 5 | 4.2 | >99 |

Example 11: Activity of Omega-Transaminase Mutants Including W58 Point Mutation Toward Various Ketoacids In order to evaluate availability of synthesis of optically pure amino acids using the omega-transaminase mutants, activity toward various ketoacids was measured using (S)-α-MBA as an amino donor.

The omega transaminase mutants including W58 point mutation purified in Example 4 was subjected to reaction under the following conditions: 10 mM (S)-α-MBA, 10 mM ketoacid, 50 mM phosphate buffer pH 7, and 37° C. Results are shown in the following Table 14.

TABLE 14

| Ketoacids | Relative activity | | | |
|---|---|---|---|---|
| | OATA WT | OATA L57A | OATA L57A/W58A | OATA L57A/W58A/V154A |
| pyruvic acid | 100% | 77% | 707% | 1,190% |
| 2-oxobutanoic acid | 17.2% | 34% | 290% | 852% |
| 2-oxopentanoic acid | 0.6% | 40% | 103% | 206% |
| 2-oxohexanoic acid | 1% | 15% | 49% | 114% |
| 2-oxooctanoic acid | 1% | 2% | 7% | 21% |
| 3-methyl-2-oxobutyric acid | n.d. | | n.d. | 11% |

When a W58 point mutation is further introduced on OATA L57A, reactivity of various ketoacids was improved, in particular, in the case of 2-oxobutanoic acid, reaction rate was increased by 8- and 25-fold in OATA L57A/W58A and OATA L57A/W58A/V154A respectively, as compared to OATA L57A. In addition, OATA L57A/W58A/V154A exhibited activity even to 3-methyl-2-oxobutanoic acid which did not react with OATA WT.

As apparent from the above description, the present invention provides omega-transaminase mutants which exhibit higher activity toward various substrates than OATA WT and a method for producing optically active amines using omega-transaminase mutants.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An isolated omega-transaminase mutant of a wild-type omega-transaminase having the amino acid sequence of SEQ ID NO: 1 for producing an optically active amine from a ketone substrate,
   wherein the omega-transaminase mutant has a point mutation at position 58 rendered by replacing tryptophan with a first different amino acid selected from the group consisting of alanine, cysteine, histidine, isoleucine, leucine, methionine, asparagine, glutamine, serine, threonine, valine, and tyrosine; and
   wherein the omega-transaminase mutant has up to ten additional point mutations.

2. The isolated omega-transaminase mutant according to claim 1, wherein the isolated omega-transaminase mutant has an amino acid sequence selected from the group consisting of the amino acid sequences of SEQ ID NOS: 2 to 6 and 11 to 15.

3. An isolated omega-transaminase mutant of a wild-type omega-transaminase having the amino acid sequence of SEQ ID NO: 1 for producing an optically active amine from a ketone substrate,
   wherein the omega-transaminase mutant has a point mutation at position 58 rendered by replacing tryptophan with a first different amino acid,
   wherein the omega-transaminase mutant has a second point mutation rendered by replacing at least one amino acid selected from the group consisting of leucine at position 57, valine at position 154, and isoleucine at position 261,
   wherein the isolated omega-transaminase mutant has an amino acid sequence selected from the group consisting of the amino acid sequences of SEQ ID NOS: 20 and 27 to 30; and
   wherein the omega-transaminase mutant has up to ten additional point mutations.

4. The isolated omega-transaminase mutant according to claim 1, further comprising a second point mutation,
   wherein a second point mutation is rendered by replacing at least one amino acid selected from the group consisting of tyrosine at position 20, methionine at position 54, leucine at position 57, phenylalanine at position 86, valine at position 154, alanine at position 230, valine at position 233, isoleucine at position 261, threonine at position 324 and isoleucine at position 380 with a second different amino acid.

5. The isolated omega-transaminase mutant according to claim 4, wherein the isolated omega-transaminase mutant has an amino acid sequence selected from the group consisting of the amino acid sequences of SEQ ID NOS: 20 and 27 to 30.

6. The isolated omega-transaminase mutant according to claim 1, wherein the isolated omega-transaminase mutant has the amino acid sequence of SEQ ID NO:2.

7. The isolated omega-transaminase mutant according to claim 1, wherein the isolated omega-transaminase mutant consists of 456 amino acids.

8. The isolated omega-transaminase mutant according to claim 1, wherein the isolated omega-transaminase mutant has at least 97% homology with SEQ ID NO:1.

* * * * *